(12) United States Patent
Park et al.

(10) Patent No.: US 7,179,500 B2
(45) Date of Patent: Feb. 20, 2007

(54) SUB-MICRON ELECTROLYTE THIN FILM ON NANO-POROUS SUBSTRATE BY OXIDATION OF METAL FILM

(75) Inventors: Yong-Il Park, Kyungbuk (KR); Friedrich B. Prinz, Woodside, CA (US); Suk-Won Cha, Stanford, CA (US); Sang-Joon John Lee, Sunnyvale, CA (US); Yuji Saito, Palo Alto, CA (US)

(73) Assignees: The Board of Trustees of the Leland Stanford Junior University, Palo Alto, CA (US); Honda Giken Kogyo Kabushiki Kaisha, Tokyo (JP)

(*) Notice: Subject to any disclaimer, the term of this patent is extended or adjusted under 35 U.S.C. 154(b) by 265 days.

(21) Appl. No.: 10/449,736

(22) Filed: May 29, 2003

(65) Prior Publication Data

US 2004/0013924 A1 Jan. 22, 2004

Related U.S. Application Data

(60) Provisional application No. 60/384,380, filed on May 29, 2002, provisional application No. 60/384,378, filed on May 29, 2002.

(51) Int. Cl.
*B05D 5/12* (2006.01)
*H01M 4/82* (2006.01)
*C23C 14/00* (2006.01)

(52) U.S. Cl. ............... 427/115; 427/383.1; 427/383.5; 29/623.5; 204/192.12; 204/192.15

(58) Field of Classification Search ................ 427/115, 427/383.1, 383.5; 29/623.5; 204/192.15; 429/30, 33
See application file for complete search history.

(56) References Cited

U.S. PATENT DOCUMENTS 4,764,491 A 8/1988 Quadir ....................... 501/103

(Continued)

FOREIGN PATENT DOCUMENTS

JP 03-064087 3/1991

(Continued)

OTHER PUBLICATIONS

Mukherjee, Amit et al., "Correlation between slurry rheology, green density and sintered density of tape cast yttria stabilized zirconia," Ceramics International 27 (2001), p. 731-739.

(Continued)

*Primary Examiner*—Brian K. Talbot
(74) *Attorney, Agent, or Firm*—Lumen Intellectual Property Services

(57) ABSTRACT

A fluid impermeable thin film is fabricated on a porous substrate by depositing a material having a certain spatial oxidation expansion. After deposition, the material is oxidized whereby the deposited material expands and forms a void free film on top of the porous substrate. The snuggly contacting grain boundaries of the void free film may recombine to a continuous thin film that has a thickness of only a fraction of 1 μm and is substantially fluid impermeable. The small film height contributes to a high ionic conductivity that makes the thin film a preferred choice for a fuel cell electrolyte membrane enabling efficient fuel cell operation at temperatures well below 500° C.

10 Claims, 19 Drawing Sheets

U.S. PATENT DOCUMENTS

| | | | |
|---|---|---|---|
| 4,839,019 A | 6/1989 | Takahama et al. | 204/425 |
| 4,888,114 A | 12/1989 | Gaddis et al. | 210/500 |
| 5,106,654 A | 4/1992 | Isenberg | 427/115 |
| 5,130,210 A | 7/1992 | Iwasaki et al. | 429/33 |
| 5,160,618 A | 11/1992 | Burggraaf et al. | 210/490 |
| 5,250,184 A | 10/1993 | Maier | 210/653 |
| 5,344,549 A | 9/1994 | Dees | 204/425 |
| 5,387,541 A | 2/1995 | Hodge et al. | 437/71 |
| 5,415,891 A | 5/1995 | Liu et al. | 427/243 |
| 5,439,706 A * | 8/1995 | Richards et al. | 427/244 |
| 5,534,471 A | 7/1996 | Carolan et al. | 502/4 |
| 5,681,373 A | 10/1997 | Taylor et al. | 96/11 |
| 5,782,959 A | 7/1998 | Yang et al. | 96/11 |
| 5,871,650 A | 2/1999 | Lai et al. | 210/653 |
| 6,007,683 A * | 12/1999 | Jankowski et al. | 204/192.17 |
| 6,152,987 A | 11/2000 | Ma et al. | 95/56 |
| 6,251,473 B1 | 6/2001 | Wang et al. | 427/126.3 |
| 6,432,308 B1 | 8/2002 | Gill | 210/500.25 |
| 6,465,365 B1 | 10/2002 | Annapragada | 438/763 |
| 6,514,881 B1 | 2/2003 | Coffman | 438/780 |
| 6,921,557 B2 * | 7/2005 | Jacobson et al. | 427/376.1 |
| 2003/0003348 A1 | 1/2003 | Hanket | 429/44 |

FOREIGN PATENT DOCUMENTS

JP  08-293310  * 11/1996

OTHER PUBLICATIONS

Albano, Maria P. et al., "Influence of the slip composition on the aqueous processing and properties of yttria stabilized zirconia green tapes," Ceramics International (2005).

Zhu, Qingshan et al., "Low temperature sintering of 8YSZ electrolyte film for intermediate temperature solid oxide fuel cells," Solid State Ionics 176 (2005) p. 889-894.

* cited by examiner

SUB-MICRON ELECTROLYTE THIN FILM ON NANO-POROUS SUBSTRATE BY OXIDATION OF METAL FILM

PRIORITY CLAIM

The present invention claims priority to the U.S. provisional application titled "Solid oxide electrolyte with ion conductivity enhancement by dislocation", filed May 29, 2002, application Ser. No. 60/384,378, which is hereby incorporated by reference.

The present invention also claims priority to the U.S. provisional application titled "Sub-micron Electrolyte Thin Film on Nano-Porous Substrate by Oxidation of Metal Film", filed May 29, 2002, application Ser. No. 60/384,380, which is hereby incorporated by reference.

CROSS REFERENCE

The present invention cross references the concurrently filed U.S. application Ser. No. 10/449,709, filed May 29, 2003 titled "Solid oxide electrolyte with ion conductivity enhancement by dislocation" by Yuji Saito, Fritz B. Prinz, Yong-il Park & Ryan O-Hayre, which is hereby incorporated by reference.

FIELD OF INVENTION

The present invention relates generally to electrochemical devices and methods. More particularly, the present invention relates to solid oxide fuel cells [SOFC].

BACKGROUND

A fuel cell is an electrochemical device that produces electrical current from chemical reactions. The fundamental device includes an ion-conducting electrolyte between two electrodes, backed by fuel and oxidant flow distributors. A catalyst on one electrode promotes separation of ions and electrons at the oxidant side. Only the ions conduct through the electrolyte, and recombine with electrons at the fuel side. The electrons are conducted through an external circuit, thus supplying electrical power. Solid oxide fuel cells have ionic-conducting metal oxide membranes as their electrolyte layer. The oxygen molecules are split into their respective electrons and oxygen ions at the airside. The oxygen ions propagate through the electrolyte membrane and combine with their electrons and hydrogen molecules into water.

Fuel cell operation is increasingly efficient where the well-known electron conductivity of the electrolyte is brought to a minimum and the well-known ionic conductivity of the electrolyte is brought to a maximum. At the same time it is desirable to keep the fuel cell's driving temperature as low as possible such that the well-known thermodynamic efficiency and the well-known electric load responsiveness of the fuel cell remains at high levels.

As is well-known in the art, ohmic resistance and ionic conductivity of conventional electrolyte materials vary with electrolyte temperature. In that context, Table 1 lists exemplary values of ionic conductivity $\sigma$ [S/cm], ohmic resistance of electrolyte film at 1 $cm^2$ of area and at given film thickness R [$\Omega$] for various yttria stabilized zirconium [YSZ] film, thickness of various YSZ film h [$\mu$m, nm] and temperatures t.

TABLE 1

| t [° C.] | $\sigma$ [S/cm] | R [$\Omega$] for h = 5 $\mu$m | R [$\Omega$] for h = 500 nm | R [$\Omega$] for h = 200 nm | R [$\Omega$] for h = 20 nm |
|---|---|---|---|---|---|
| 503 | 0.001 | 0.5 | 0.005 | 0.02 | 0.002 |
| 422 | 1.58e−4 | 3.1 | 0.31 | 0.12 | 0.01 |
| 360 | 3.00e−5 | 16.6 | 1.66 | 0.66 | 0.07 |
| 322 | 8.00e−6 | 62.5 | 6.25 | 2.5 | 0.25 |
| 250 | 5.11e−7 | 978 | 97.8 | 39.1 | 3.9 |
| 200 | 4.54e−8 | 11010 | 1101 | 440 | 44 |
| 100 | 4.88e−11 | 10245900 | 1024590 | 409836 | 40983 |

The bold and italic entries of Table 1 indicate ohmic values relevant for efficient fuel cell operation. Hence, by reducing the electrolyte height, the driving temperature, the ohmic resistance and the ionic conductance are reduced as well.

At the time the present invention was made, extensive effort has been dedicated to reduce electrolyte thickness. In one well-known tape casting technique for example, slurry of submicrometer-sized powders is used to produce highly dense and mechanically strong electrolyte films with good electrical properties. Unfortunately, the electrolyte films are fabricated only with relatively large heights in the range of hundreds of micrometers. This reduces the ionic conductance across the electrolytes' heights to relatively low levels that may be only partially compensated by high working temperatures of 800–1000° C.

In another approach, electrolyte films are fabricated as anode-supported thin oxide films with electrolyte heights between 5–20 $\mu$m resulting in a working temperature range of 500–1000° C. Even though a significant reduction of the lower working temperature limit was accomplished, 500° C. require still significant constructive effort and limit the feasibility of such a fuel cell for practical applications.

At the time of the invention, high-tech processing such as well-known PVD, CVD, PLD and sol-gel deposition has been tested to further reduce electrolyte thickness and increase film density. Since the electrolyte operates also as a membrane that physically separates reactant fluids within the fuel cell, film density becomes more important with decreasing electrolyte thickness to provide gas impermeability at sufficiently high levels. Unfortunately, the high-tech deposition technologies have been developed mainly for highly flattened substrates, especially silicon wafers. To the contrary, a substrate qualifying for deposition of an electrolyte membrane must be highly gas permeable to provide for fluid conductance through the substrate and for a direct fluid contact with the electrolyte at the electrolyte side adjacent the substrate. A qualifying substrate needs to be highly porous, which results in a relatively rough, discontinuous and inhomogeneous surface on a scale similar to that of the electrolyte's film height.

A successful deposition of continuous submicron YSZ thin films on anodized nanoporous alumina has been demonstrated in the prior art by a sol-gel deposition technique using viscous alkoxide-derived solution applied on top of the porous substrate. However, sol-gel derived thin films exhibit a large shrinkage during heat-treatment and low density from inherent high organic content that may cause local defects. Consequently, continuous films that are substantially fluid impermeable may not be fabricated with sol-gel deposition techniques.

In summary, prior art oxide film deposition techniques are not suitable in combination with a qualifying substrate. Therefore, there exists a need for a fabrication technique for making an operational electrolyte membrane on top of a porous substrate. The present invention addresses this need.

In general, an electrolyte layer of a solid oxide fuel cell should have the following properties:
  high ionic conductivity, which means also low ionic resistance;
  low electron conductivity, preferably by reduction of thickness;
  high density and impermeability to prevent electric potential drop between both sides of the electrolyte layer due to reactant fluid mixture;
  sufficient mechanical strength at operational fluid pressures; and
  good adhesion to electrode layers to reduce resistance between electrolyte and electrode for increased fuel cell efficiency and to prevent second phase formation.

The present invention addresses these general needs.

In particular, an electrolyte layer is needed that may be fabricated in an inexpensive fashion with a configuration that provides for an efficient fuel cell operation at working temperatures of 500° C. and substantially less. The present invention addresses also these needs.

SUMMARY

The present invention provides for new functional solid oxide fuel cell assemblies. The present invention is based on a different set of materials and processes for manufacturing functional solid oxide fuel cell assemblies compared to previous devices or methods. In summary, the present invention provides a direct metal film deposition to obtain ultra-thin oxide film by oxidation. Furthermore, the present invention utilizes a porous substrate (e.g. a nanoporous anodized alumina substrate) as a supporting material for electrolyte thin film. A preferred embodiment of the present invention is based on:
  1. Selecting a deposition material having a certain spatial oxidation expansion. The selected material may include a metal alloy and/or individual metals a prepared as a complex metal sputtering target. Such a complex metal sputtering target may be, for example yttrium pieces allocated on Zr target for direct deposition of metal Yttrium-Zirconium layer.
  2. Depositing the deposition material in unoxidized condition directly on the porous substrate. To utilize increased ionic conductivity along grain boundaries without degrading parasitic capacitances it is desirable to deposit the material with single grain height such that ions may propagate along continuous grain boundaries between opposing sides of the final continuous film. The sputtering parameters may be adjusted accordingly and in a well-known fashion. An exemplary deposition of the Yttrium-Zirconium layer may be accomplished by DC-magnetron sputtering on a porous gamma alumina substrate in Ar atmosphere. Even though the deposited material may optically appear a solid surface, microscopic grain boundaries and voids make the deposited layer highly fluid permeable.
  3. Oxidizing the deposited material in any suitable fashion. For example, the Yttrium-Zirconium layer may be oxidized in an oxidizing atmosphere at a temperature between 300° C.~1000° C. The spatial expansion that the deposited material undergoes while it is oxidized causes the formation of a void-free film.
  4. Heat treatment of the void-free film for controlled grain modification including grain growth. Grain growth during heat treatment is not associated with a spatial expansion like during oxidation. Grain growth during heat treatment results from recombination of individual grains whereby eventual residual voids are eliminated.

In fuel cells where it is desired to have the electrolyte film as thin as possible, the simple and inexpensive fabrication of ultra thin fluid impermeable electrolyte films is highly advantageous for providing a highly efficient fuel cell that may be operated at a low working temperature well below 500° C.

Some of the advantages of the present invention over existing devices and methods include:
  1. A decrease of electrolyte resistance that is enabled by the use of the above and below described metal-oxidized electrolyte thin film processes in combination with porous substrates such as nano-porous anodized alumina substrate or other well-known porous metallic and/or ceramic substrates such as porous silicon.
  2. A simple and clean fabrication that is enabled by the use of well-known thin film deposition techniques such as DC-magnetron sputtering processes in Ar gas.
  3. Flexible fabrication costs, which are provided by a broader choice of deposited materials such as relatively inexpensive Yttrium and Zirconium alloy or complex target compared to high-cost yttria stabilized zirconia target.

DETAILED DESCRIPTION

Two factors mainly influence the operational configuration of a continuous ultra thin film. A first factor is fabrication feasibility. A second factor is operational structure considerations. In the case where the continuous ultra thin film is utilized as a membrane, fluid impermeability becomes a third influencing factor. In case, where the continuous ultra thin film is utilized as an electrolyte, ionic conductivity becomes a fourth influencing factor.

Figure 1:
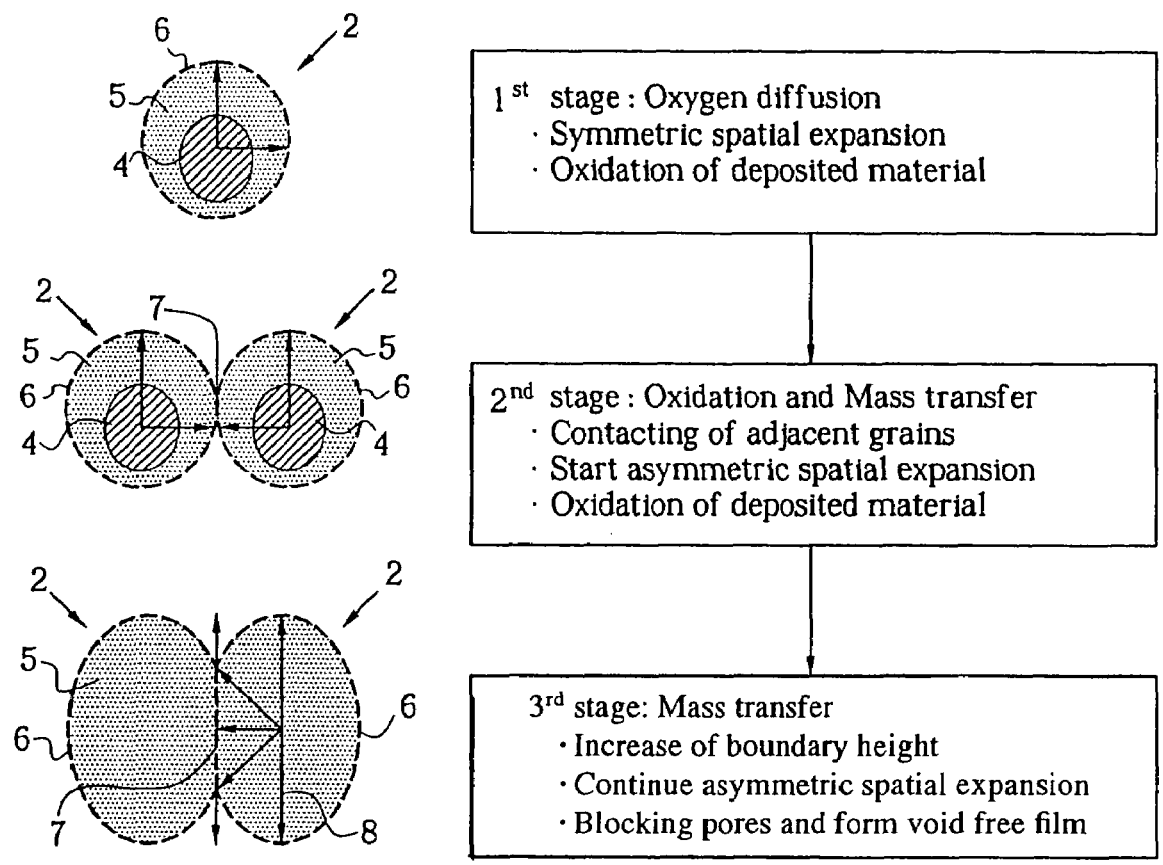
FIG. 1 illustrates the inventive utilization of spatial expansion during oxidation with a block diagram and associated schematic. The schematic on the left side of FIG. 1 depicts simplified material grains in a frontal cut view.

Referring to FIG. 1 and in compliance with the first factor, the present invention takes advantage of a spatial oxidation expansion, which a deposited material 4 may undergo during an oxidation process. The spatial oxidation expansion may be broken down into three stages. During a first stage of sole oxygen diffusion, the grains 2 expand substantially symmetric during oxidation of the deposited material 4. Symmetric spatial expansion takes place as long as the expansion remains physically uninhibited. Oxidized material 5 begins to progress from the grain boundary 6 towards the grain center continuously replacing the deposited material 4.

Once adjacent grains 2 come into contact, a second stage including a mass transfer is initiated. During the second stage, an asymmetric spatial expansion takes place while the oxidation of the deposited material 4 continues towards the grain centers. The asymmetric spatial expansion stems from the restricted expansion in the grain interface 7 between the adjacent grains 2. During the second stage, eventual voids and pores between adjacent grains 2 are filled with the expanding oxidized material. Voids and pores are likely resulting from initial deposition of the grains 2.

Once all deposited material 4 is oxidized, the spatial oxidation expansion discontinues. Due to high temperature, mass transfer may still continue and voids and pores between adjacent grains 2 are filled with oxidized material 5. Excess material is urged along the grain boundaries 6 resulting also in an increase of height 8. At the end of the three stages oxidation process, a void free film is formed.

A spatial oxidation expansion ratio between the unoxidized material and the oxidized material may be readily predetermined in a well-known fashion. In the exemplary case of unoxidized Aluminum (FCC, a=4.049 Å) as the deposited material 4 and well-known Alpha Alumina (HCP, a=4.758 Å, c=12.99 Å) as the oxidized material 5, the spatial oxidation expansion ratio is 1.279. In the exemplary case of an 85/15 Zirconium/Yttrium alloy (HCP, a=3.232 Å, c=5.147 Å) as the deposited material 4 and cubic yttria stabilized zirconia (FCC, a=5.139 Å) as the oxidized material 5, the spatial oxidation expansion ratio is 1.45.

Important for obtaining a void free film is the oxidization expansion of the deposited grains within the deposition plane. The in plane portion of the spatial oxidation expansion ratio may calculated as the second power of the third root of the spatial oxidation expansion ratio. Hence, the in-plane oxidation expansion ratio for unoxidized Aluminum to oxidized Alpha Alumina is about 1.178. The in-plane oxidation expansion ratio for unoxidized 85/15 Zirconium/Yttrium alloy to yttria stabilized zirconia is about 1.131. As may be well appreciated by anyone skilled in the art and in order to obtain a void free film, an in-plane deposition density of the deposited material may be at least the inverse of the in-plane oxidation expansion ratio. In that context, in-plane deposition density refers to the average ratio between voids and deposited grains 2 across a deposition height of the deposited grains 2. Accordingly, the deposition density for unoxidized aluminum may be at least about 0.849 and for unoxidized 85/15 Zirconium/Yttrium alloy may be at least about 0.78.

The three-stage oxidization is preferably performed at temperatures well above an operational temperature of the finally fabricated continuous film. An oxidization temperature is selected such that the deposited material and/or the oxidized material is/are in a condition of increased plasticity. The increased plasticity in turn is important for the mass transfer. YSZ is oxidized preferably at temperatures between 300°~400° C.

Figure 2:
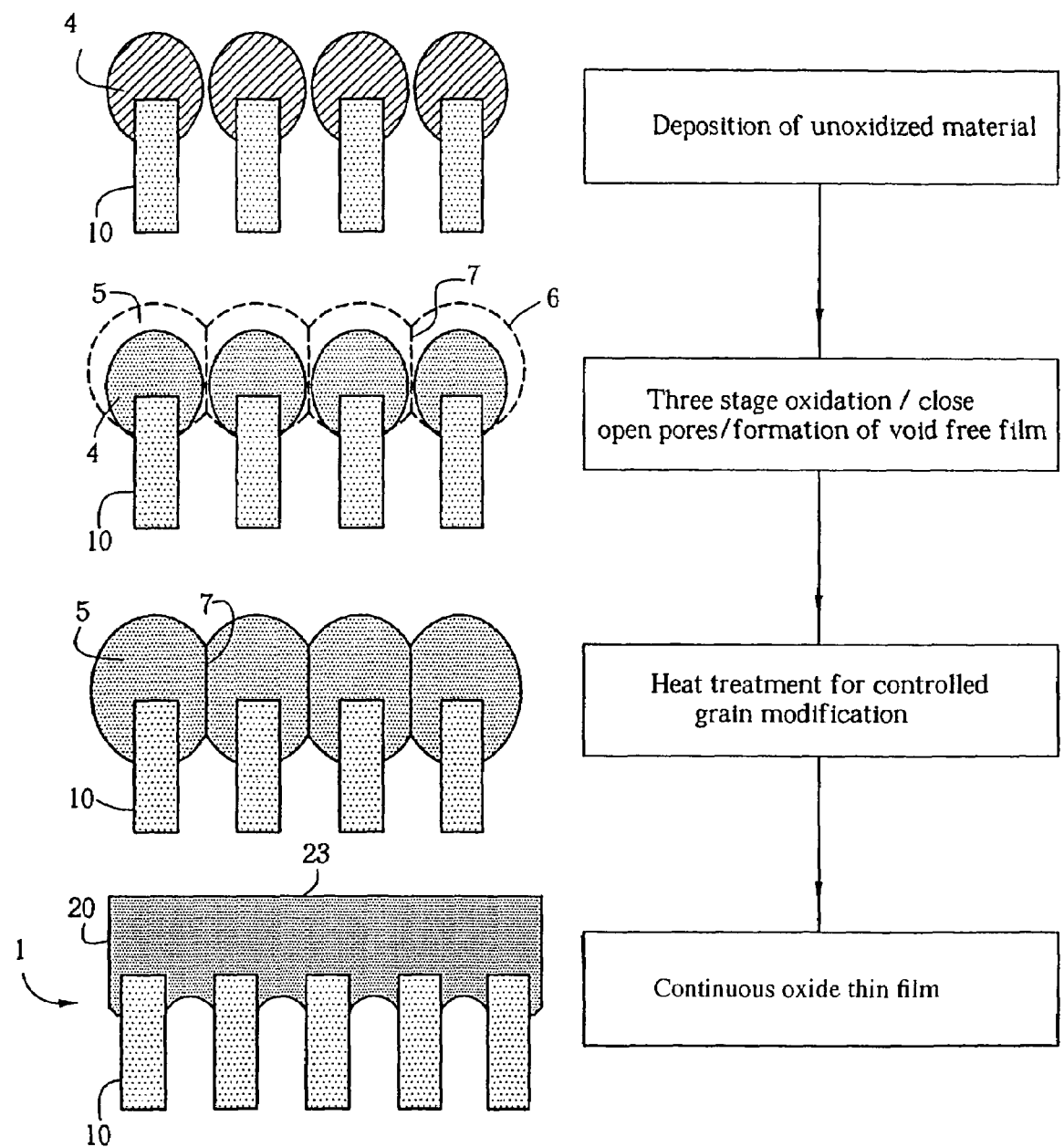
FIG. 2 schematically depicts the steps for fabrication of a continuous film on a porous substrate with associated block diagram.

FIG. 2 illustrates the application of the three-stage oxidization in fabrication of a continuous film 20 on top of a porous substrate 10. The schematic on the left side of FIG. 2 depicts a simplified frontal cut view through the porous substrate 10 with three stage oxidation and a final heat treatment step.

Initially, the material 4 is deposited in a substantially unoxidized condition on top of the solid portion of the porous substrate 10. A preferred deposition material may be a metal and a preferred deposition technique may be a well-known DC-magnetron sputtering. The porous substrate 10 may be, for example a 200 nm-type Gamma Alumina substrate with vertically protruding pores having a diameter between 150~200 nm (see FIG. 4). The 200 nm-type porous substrate may have a void/solid ratio of about 9/1, which means that about 10% of the porous substrate's 10 top are solid and the remaining about 90% of the porous substrate's 10 top are open.

Figure 5:
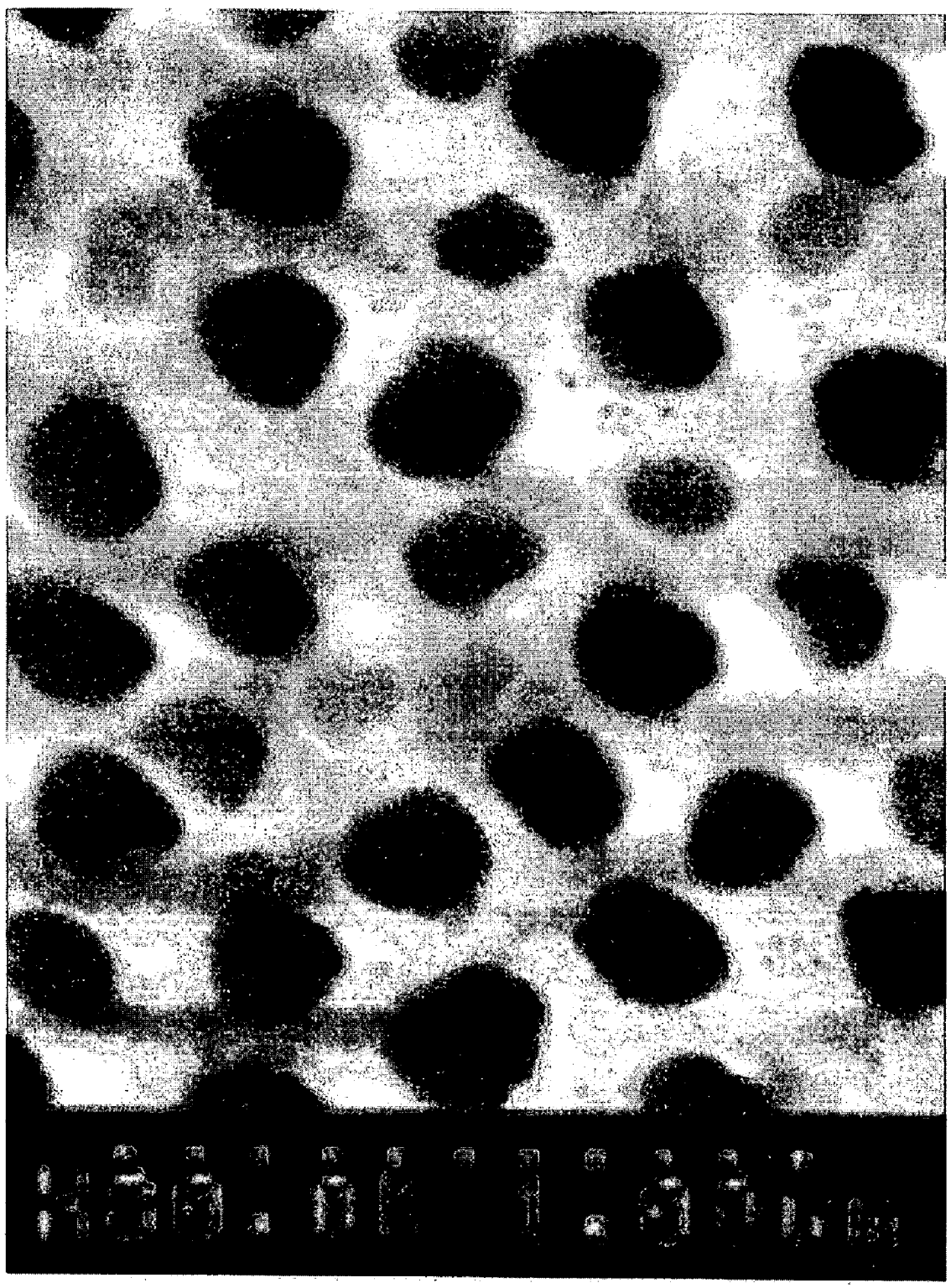
FIG. 5 is an enlarged picture of the top of a 20 nm-type gamma alumina nanoporous substrate.

The porous substrate 10 may also be, for example a 20 nm-type Gamma Alumina substrate with vertically protruding pores having a diameter between 80~200 nm (see FIG. 5). The 20 nm-type porous substrate may have a void/solid ratio of about 1/1, which means that about 50% of the porous substrate's 10 top are solid and the remaining about 50% of the porous substrate's 10 top are open. Porous substrate 10 made from Gamma Alumina may be commercially available under the tradename Anodisc®.

To fabricate the final continuous film 20 with minimum thickness, the initial deposition step is adjusted to provide the required deposition density while keeping the deposition height to a minimum. As the void/solid ratio of the porous substrate 10 increases, deposition density becomes more challenging to accomplish for a targeted deposition thickness. For example, to deposit Aluminum on a 200 nm type porous substrate 10 with required deposition density, about 11.8% of the deposited material 4 is directly supported by the solid portion of the porous substrate 10. This example is solely presented for the purpose of general understanding of the structure considerations that exist for optimized deposition of material 4 on top of the porous substrate 10.

In the preferred case of a DC-magnetron sputtering, deposition thickness may be minimized by adjustment of deposition parameters, such as for example, sputtering angle and/or kinetic energies of the sputtered material.

Following the deposition of the unoxidized material 4, the three stage oxidation is performed as described under FIG. 1 resulting in a void free film. In a final fabrication step, the void free film is heat treated for recombining the oxidized grains along the grain boundaries 6. In addition, the heat treatment process may be utilized to smoothen the top surface 23 of the continuous film 20. Heat may be applied as directional radiation heat and/or as convective heat. Heat treatment is preferably accomplished in a furnace.

The heat treatment step may be performed at the same and/or different temperature or atmospheric settings than applied during oxidation. Nevertheless, oxidation and heat treatment may overlap, since grain recombination may take place as soon as adjacent grain boundaries 6 expand into contact.

Figure 3A:
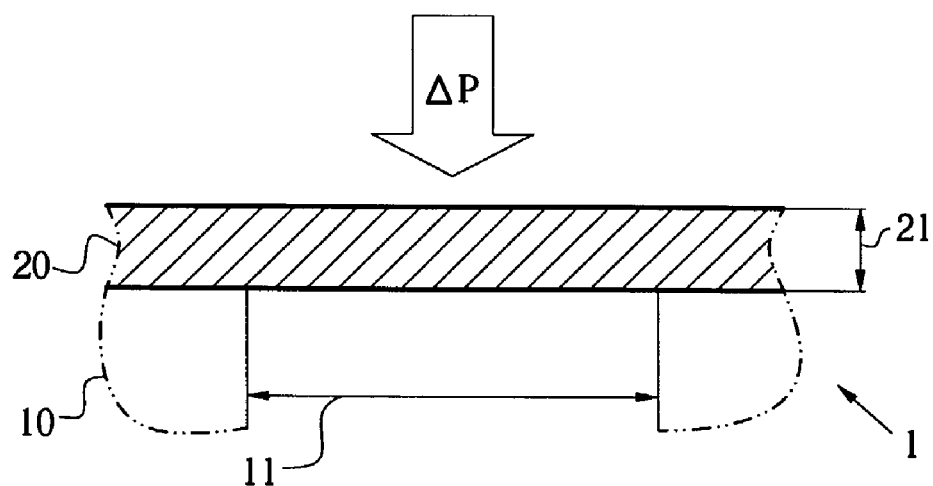
FIGS. 3a, 3b, 3c show schematic cut view portions of exemplary interfaces between continuous film and porous substrate.
Figure 3B:
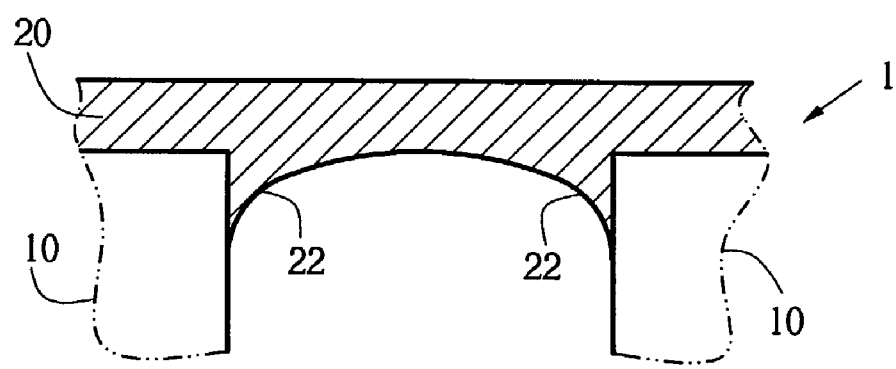

Referring to FIGS. 3a, 3b operational structure considerations for minimizing the height 21 of the continuous film are described in more detail. In context with the present invention, operational structure considerations relate to the minimum continuous film structure required for a given porous substrate 10 and mechanical operation conditions to which the continuous film 20 may be exposed. The simplest case is depicted in FIG. 3a in which the continuous thin film 21 is a substantially equally thick layer. According to FIG. 3a, a minimum for the film thickness 21 may be calculated by the following equations.

$$\sigma_{max} = 3/8 \cdot \{(1+\upsilon) \cdot (\Delta P \cdot R^2)\}/t^2 \quad [1]$$

$$t = [3\{(1+\upsilon) \cdot \Delta P \ R^2\}/(8\sigma_{max})]^{1/2} \quad [2]$$

where, $\sigma_{max}$: Ultimate tensile strength
ΔP: Pressure difference
υ: Poisson's ratio
R: Pore radius
t: Film thickness The minimum film thickness for sample A (pore size: 20 nm, ΔP: 0.1 MPa) estimated with the reported mechanical properties of commercial 99.9% bulk alumina ceramics is 0.15 nm. However, there are too many differences between bulk ceramics and thin films to directly apply the values reported for bulk alumina to this estimation. Considering the difference in grain size, density, impurity, and defects, especially pore diameter and distribution, which critically affect fracture strength, the reasonable minimum thickness might be larger than the estimation. Nevertheless, the estimated thickness limit is key reference for practical optimization of the continuous film 20.

Figure 3C:
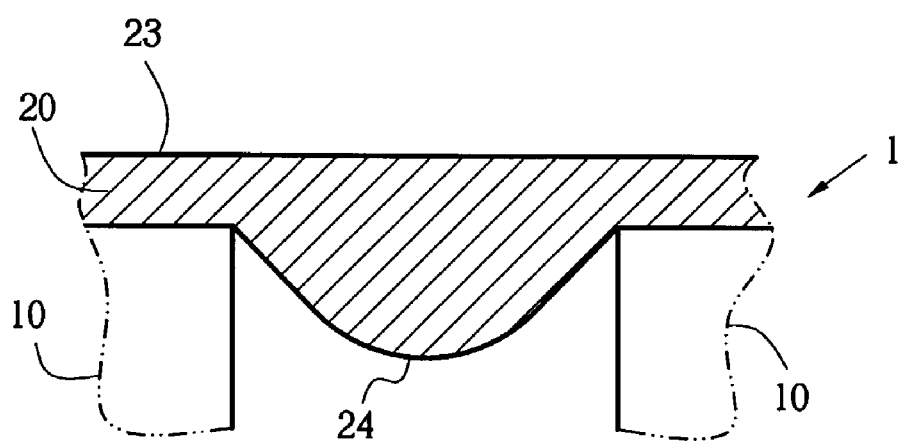

In a similar fashion as the calculations presented for the simplified case of FIG. 3a, theoretical thickness minima may be calculated for thin film configurations schematically depicted in FIGS. 3b, 3c. In FIG. 3b, the bottom portion 22 of the continuous film 20 may have a concave curvature eventually resulting from a shrinkage during cooling of the continuous film 20 after heat treatment. In addition, the film may attach laterally at the sidewalls of the substrate's 10 pores. Lateral attachment may be result from the deposition process and/or from the oxidation expansion.

Figure 10:
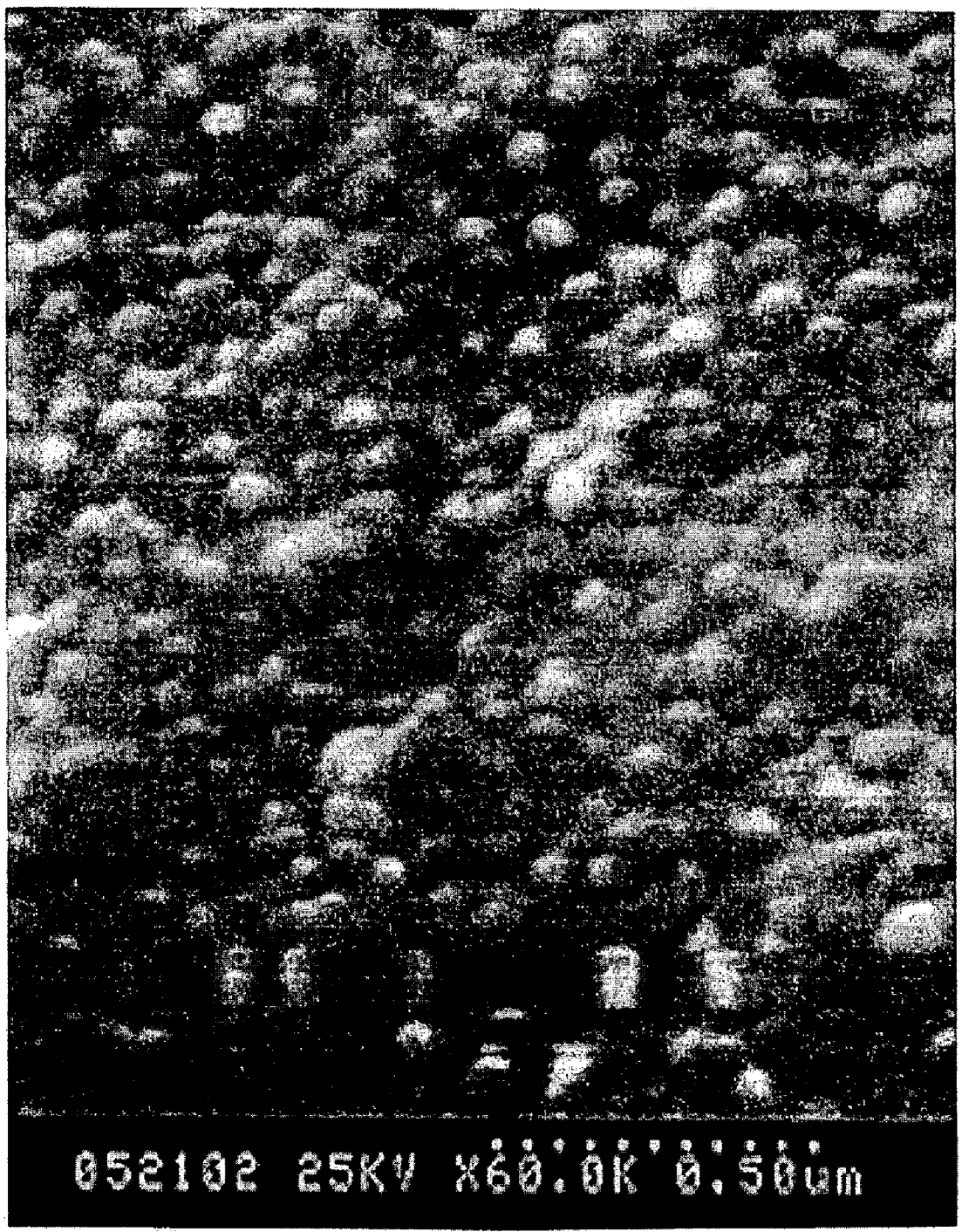
FIG. 10 is an enlarged picture of a continuous film bottom of oxidized Yttrium stabilized Zirconium layer. The substrate is etched away.

According to FIG. 3c, the bottom portion 24 may have a convex curvature eventually resulting from an excess vertical expansion. Such excess vertical expansion may result from a deposition density significantly above the required deposition density where voids and/or pores are filled significantly before the oxidation expansion is completed. The enlarged picture of FIG. 10 shows such a case.

In the following, two exemplary continuous films 20 experimentally fabricated on porous substrates 20 are described in detail. For porous substrates 10, commercial inorganic alumina filters (Anodisc®, Whatman Inc.) with a pore size of 20 nm and 200 nm were used. In context with the present invention, the terms "20 nm type" and "200 nm type" relates to terminology used by the producer with respect to the filtering ability of their respective product. The observed actual pore diameters by SEM were 80 nm~200 nm for 20 nm-type filters and 150 nm~300 nm for 200 nm-type filters. The filter diameter (without support ring) was 40 mm, filter thickness was 60 μm and maximum working pressure was about 0.52 MPa.

An Aluminum target with 99.999% purity and a Y—Zr complex target consisting of three or four 5 mm×5 mm×1 mm-sized Y pellets with 99.9% purity on a Zr target with 99.7% purity were used for metal film deposition using DC-magnetron sputtering. The Ar gas flow rate was 10 sccm and Ar pressure was 1.2 Pa at 50 W for aluminum deposition and 10 sccm~30 sccm, 1.2 Pa~2.8 Pa at 30 W for Y—Zr deposition.

After deposition of metal film, subsequent oxidation was performed at 700° C. for 2 hours in air. Two Alumina film samples with metal thickness of 30 nm and 200 nm were prepared (Table 2), and five YSZ samples were prepared with three compositions of Y/Zr (at %)=4/96, 16/84, 43/57 having different metal thickness from about 40 nm~230 nm. Thickness of the films was controlled with the deposition rate of aluminum (9.43 Å/s) and Y—Zr and was measured by using a Si wafer substrate with the same deposition condition. The composition of Y/Zr was controlled by changing location and number of Y pellet. The Y/Zr composition was determined by X-ray photoemission spectroscopy (SSI S-Probe Monochromatized XPS Spectrometer). All samples where oxidized at 700° C. for two hours. The composition of the Y/Zr samples had a purity of higher than 99.7%. The microstructure of the thin films was observed with SEM. The phase development of sample A including a separate heat-treating step at 400° C.~1300° C. for 2 hours was observed using XRD as is described in the following.

TABLE 2

| Mat. | Sample | Substrate type | Deposition condition (time-Ar flow[Pa]/pressure [Pa]-energy[W]) | Deposited thickness [nm] | Estimated thickness range of continuous film [nm] | Observed thickness of continuous film [nm] | Composition of continuous film |
|---|---|---|---|---|---|---|---|
| Al | A | 20 | 32-10/1.2-50 | 30 | 32.6–38.6 | ~35 | Al = 99.999 |
| Al | B | 200 | 212-10/1.2-50 | 200 | 217.2–257.4 | ~240 | Al = 99.999 |

TABLE 2-continued

| Mat. | Sample | Substrate type | Deposition condition (time-Ar flow[Pa]/ pressure [Pa]- energy[W]) | Deposited thickness [nm] | Estimated thickness range of continuous film [nm] | Observed thickness of continuous film [nm] | Composition of continuous film |
|---|---|---|---|---|---|---|---|
| Y—Zr | C | 20 | 400-10/1.2-50 | 38 | 43.0–55.1 | ~50 | Y/Zr = 3/97 |
| Y—Zr | D | 200 | 400-10/1.2-50 | 38 | 43.0–55.1 | ~50 | Y/Zr = 3/97 |
| Y—Zr | E | 20 | 2000-10/1.2-50 | 190 | 215.1–275.5 | ~250 | Y/Zr = 3/97 |
| Y—Zr | F | 200 | 2000-10/1.2-50 | 190 | 215.1–275.5 | ~250 | Y/Zr = 3/97 |
| Y—Zr | G | 20 | 4000-30/2.5-20 | — | — | — | Y/Zr = 43/57 |
| Y—Zr | H | 200 | 4000-30/2.5-20 | 230 | 283.0–362.0 | ~320 | Y/Zr = 16/84 |

Figure 12:
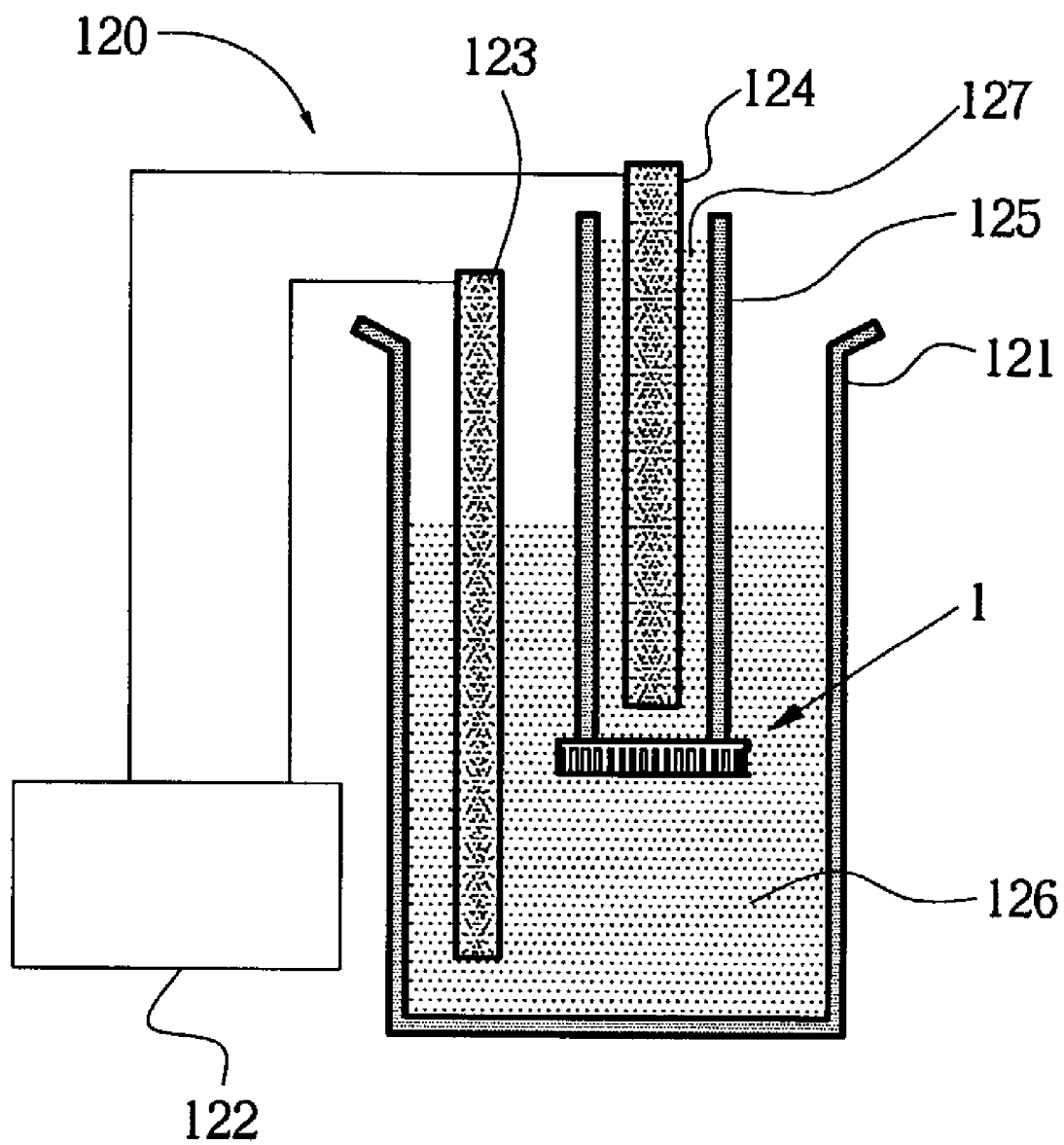
FIG. 12 depicts a schematic test setup for measuring ionic resistance of a continuous film fabricated on a porous substrate.

The samples obtained were tested in a test setup illustrated in FIG. 12. A sample 1 was fixed with polymer adhesives to a thick silicone tube 125 filled with hydrogen 127, and then immersed in NaCl-water solution 126 to measure hydrogen permeance through oxidized thin films 20. The hydrogen pressure ($\Delta P$) used was 0.1 MPa. Ionic conductivity of oxidized Y—Zr films was measured from nyquist plots obtained using 0.03N NaCl-water solution 126 as electrodes with Solartron 1260/1287 impedance analyzer 122 at room temperature.

Figure 4:
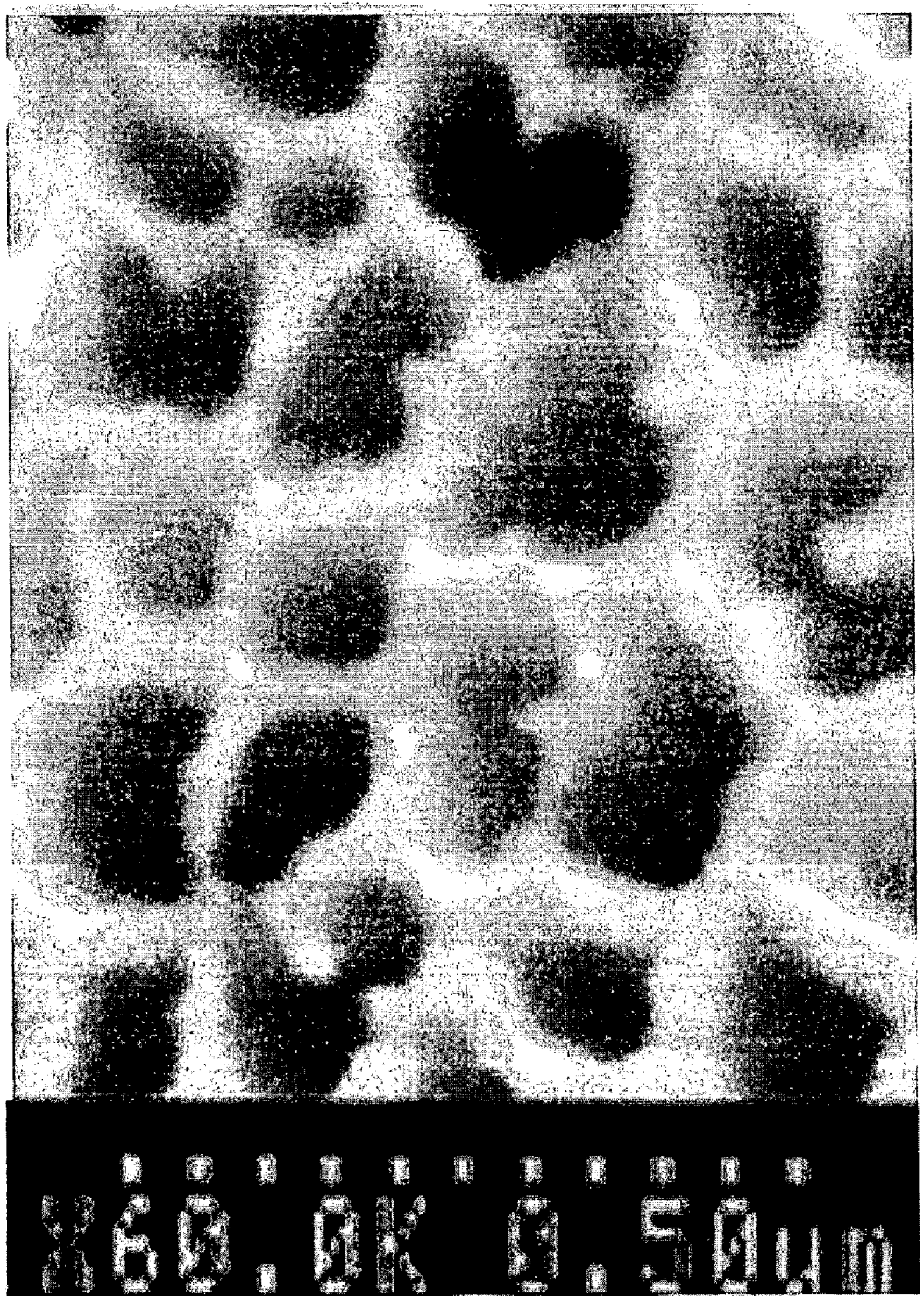
FIG. 4 is an enlarged picture of the top of a 200 nm-type gamma alumina nanoporous substrate.
Figure 6:
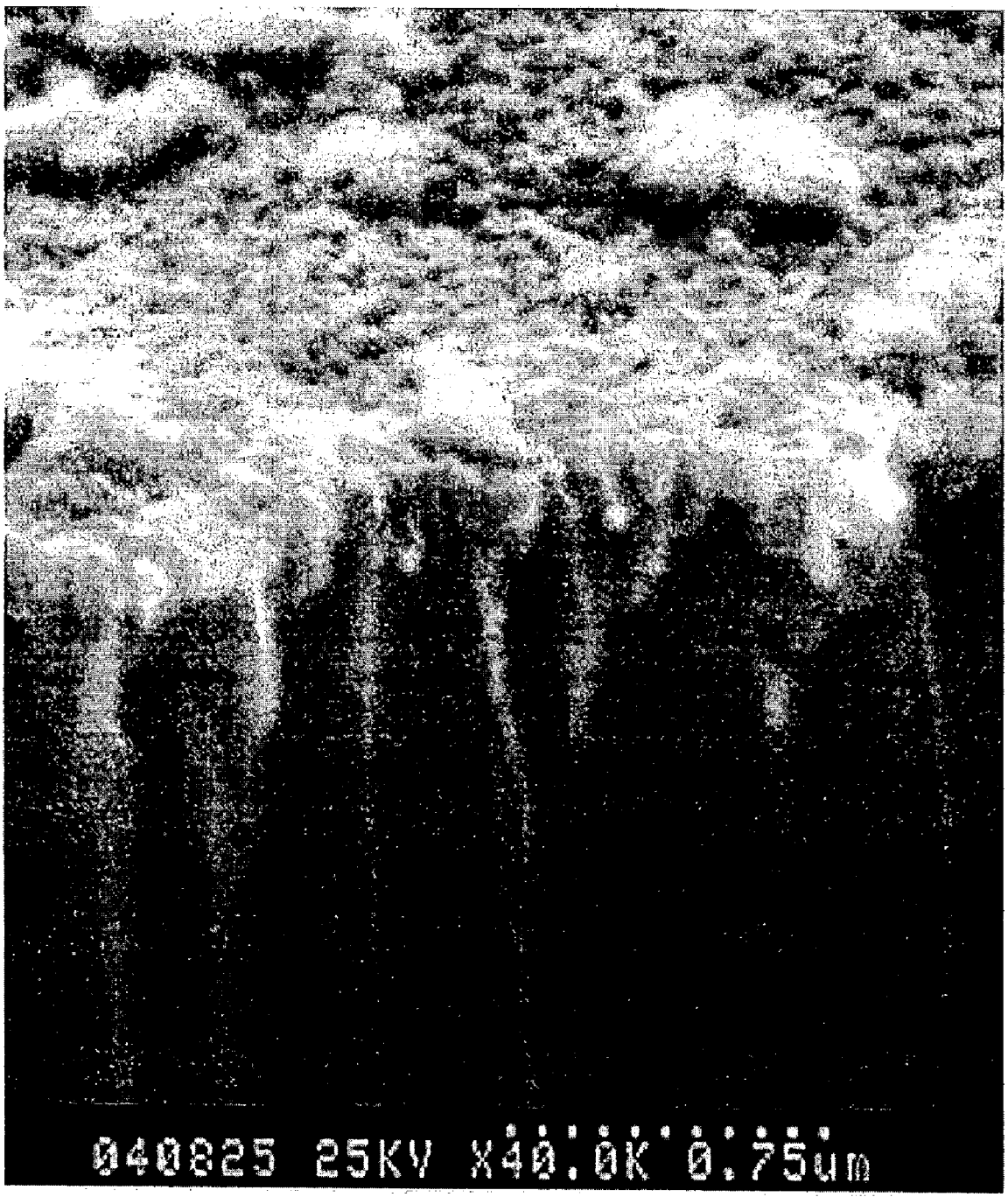
FIG. 6 is an enlarged picture of a deposited unoxidized alumina on top of a 200 nm-type gamma alumina nanoporous substrate. The continuous film and the substrate are depicted along a fracture site.

In FIGS. 4 and 5, SEM images of the Anodisc® substrates having of 200 nm-type and 20 nm-type are shown. The pores are columnar and penetrate through the porous substrates 10. FIG. 6 shows the surface and fractured edge after deposition of unoxidized aluminum on the porous substrate 10. Even though the deposited film thickness is only about 200 nm, it already covers the whole surface showing smooth and grain-like aggregated metal islands. There are also flake-shaped particles on the metal surface suggesting that impurities existed and worked as nuclei for aggregation of metal atoms during sputtering. A continuous film 20 of oxidized Aluminum was obtained from the deposited film of FIG. 6 after heat-treated at 700° C. for 2 hours. The continuous film 20 displayed a homogeneous surface covering pores of substrates without cracks or pinholes. The oxidized Aluminum film 20 may be utilized as a membrane where ionic conductivity is irrelevant. The Aluminum sample where primarily fabricated and tested for fluid impermeability and fabrication feasibility.

Figure 11A:
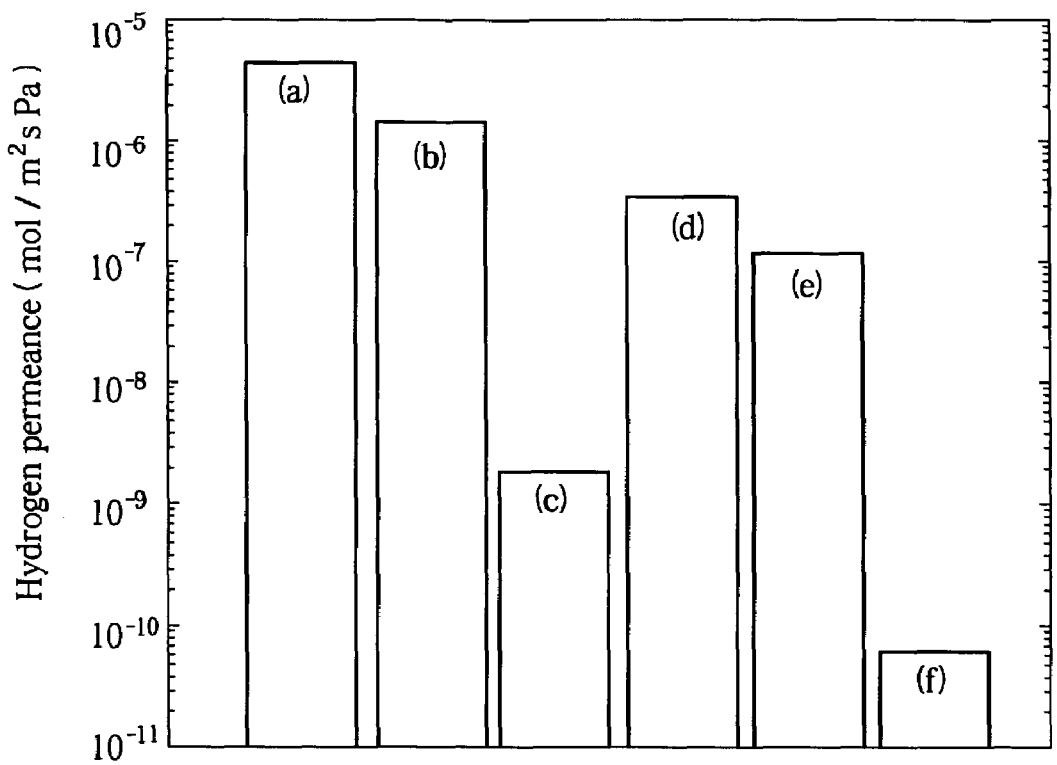
FIG. 11 shows a bar graph with hydrogen permeances for various substrate conditions and various continuous films.

Fluid impermeability was tested in a hydrogen permeation test in which the hydrogen permeance was measured at 0.1 MPa. The results are depicted in FIG. 11a. The permeance for sample B (column (a)) is $6.40 \times 10^{-6}$ mol/m²·s·Pa and slightly decreased to $1.97 \times 10^{-6}$ mol/m²·s·Pa by heat-treatment at 700° C. for 2 hours (column (b)). This may be due to change of the dimension of columns by shrinkage during heat-treatment. The permeance for sample B (with a thin film, column (c)) drastically decreased to $2.01 \times 10^{-9}$ Mol/M²·s·Pa.

The permeances measured for the sample A are reflected in columns (d), (e) and (f). They show smaller values than those of (a), (b) and (C) due to their smaller pore size. The gas permeance for sample A (column(f)) could not be detected with the present measurement settings and thus the measurable minimum permeance of $7.44 \times 10^{-11}$ mol/m²·s·Pa is assigned for column(f).

Fabrication feasibility of continuous films 20 is strongly influenced by the deposited material's 4 oxidation behavior and phase development. To observe phase development during oxidation of the thin films of samples A, B, XRD patterns at various oxidation stages and during the heat-treatment were obtained. No distinct crystalline peak was observed until the temperature reaches 900° C. However, the color of thin film changed from metal silver to glassy transparent at 500° C. At 900° C., theta-alumina phase was detected and the peak intensity increased with increasing temperature. At 1300° C. well-developed theta phase was observed. However, several peaks of alpha phase were also detected in the pattern of 1300° C. Since the film thickness was just 30 nm, the collected patterns were strongly affected by the substrate 10 and show both phases of thin film 20 and substrate 10. To determine whether or not this alpha phase was from the thin film, the XRD pattern was compared with that of a bare substrate 10 heated at 1300° C. for 2 hours. The comparison clearly showed that only the pattern from thin film showed alpha phase even though the peak intensity was small compared to that of bare substrate. The relative peak intensity estimated from the fitted alpha phase peaks matched well with the relative intensity from reported data for bulk polycrystalline alpha-alumina.

In summary, Aluminum 20 deposited with a height of about 30 nm oxidizes around 500° C. and transforms to alpha phase between 1000° C.~1300° C. Otherwise, the substrate 10 has amorphous phase up to 700° C. and then transforms to theta-form at 800° C. The protective oxide layer formed on the surface of aluminum and low oxygen diffusivity may be responsible for the high crystallization temperature observed. It was found that aluminum film with a thickness of 200 nm was not fully oxidized after 10 hours of heat-treatment at 700° C., while clear single YSZ phase was easily achieved from oxidized Y—Zr alloy deposited with a height of about 200 nm and heat-treated at 700° C. for 2 hour.

For the preferred embodiment of an electrolyte membrane in a fuel cell, continuous films 20 made of deposited Y/Zr alloy are now described in detail. A Y/Zr alloy deposited with a thickness of about 50 nm displayed in an SEM photography a silver-colored smooth surface without pores or voids being detected. The actual deposition density of the samples C–H was above the required deposition density. Consequently and as depicted in FIG. 10, the bottom of the derived continuous film 20 appeared similar to the bottom of FIG. 3c.

Figure 7:
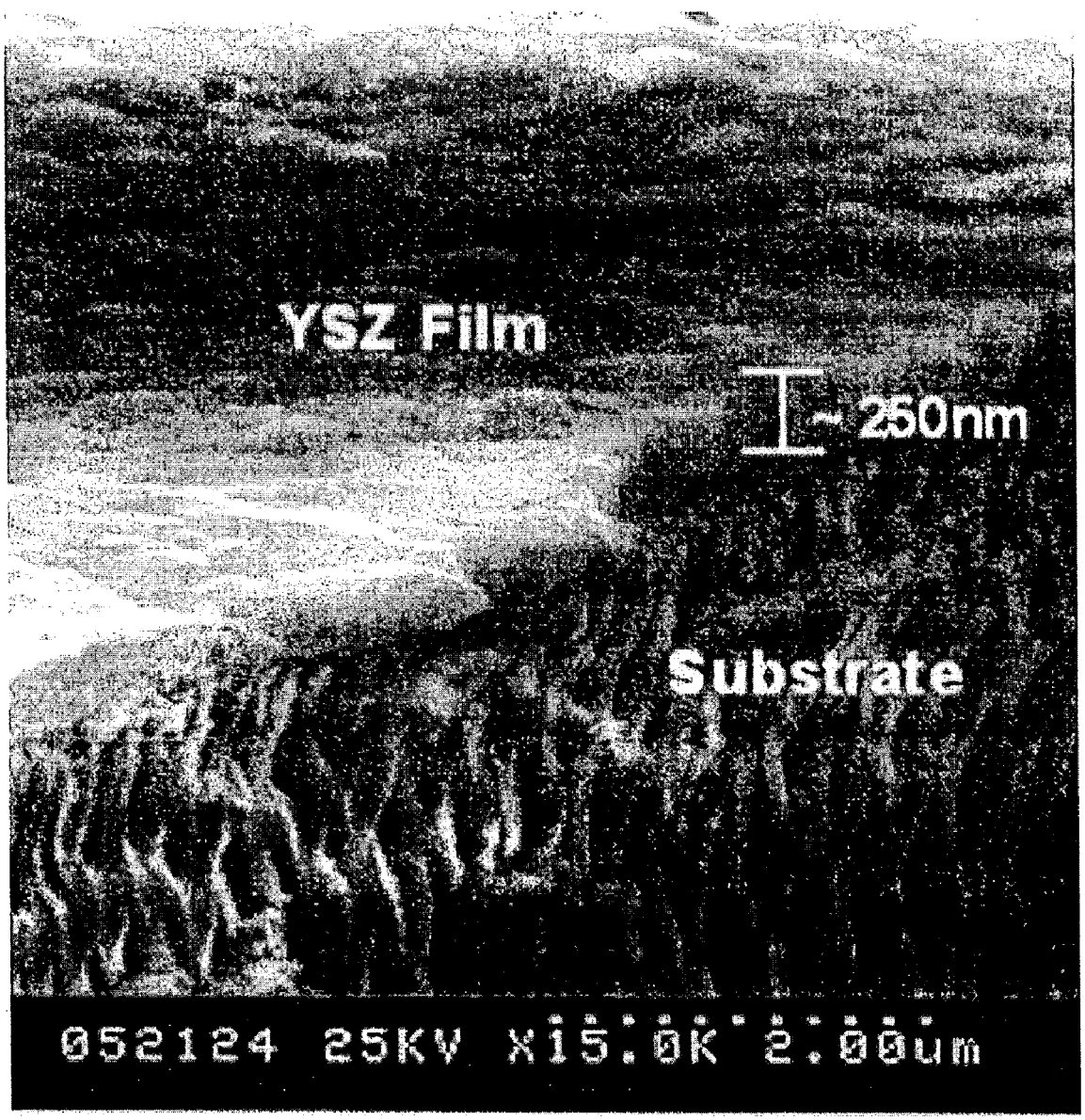
FIG. 7 is an enlarged picture of a continuous film of oxidized Yttrium stabilized Zirconium layer on top of a 200 nm-type gamma alumina nanoporous substrate. The continuous film and the substrate are depicted along a fracture site.
Figure 8:
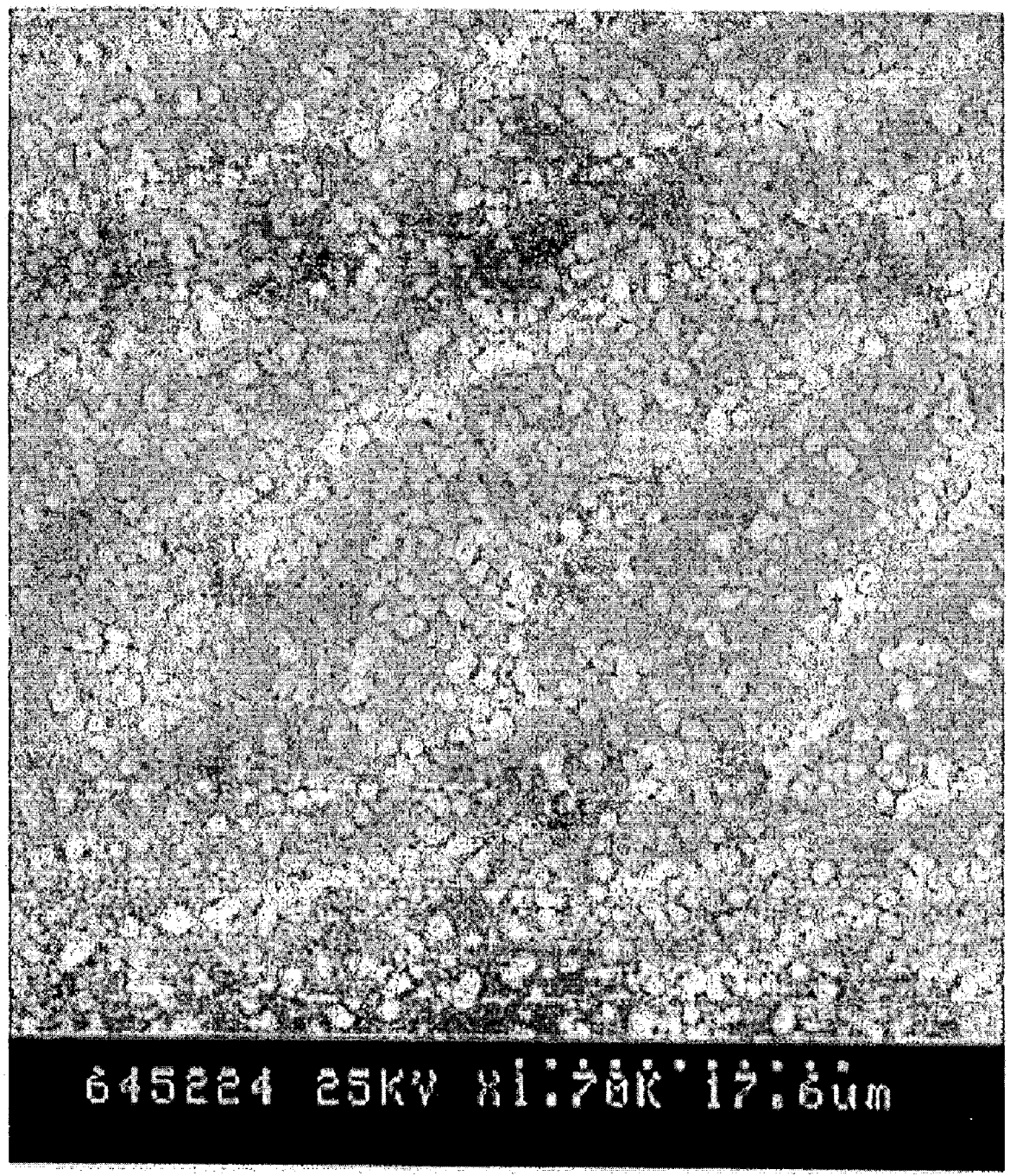
FIG. 8 is an enlarged picture of a continuous film top of oxidized Yttrium stabilized Zirconium layer.
Figure 9:
FIG. 9 is an enlarged picture of a continuous film of oxidized Yttrium stabilized Zirconium layer on top of a 20 nm-type gamma alumina nanoporous substrate. The continuous film and the substrate are depicted along a fracture site.

As shown in FIG. 7 and after oxidation and heat treatment at 700° C. for 2 h, sample E displayed a continuous film 20 without any cracks and pinholes appeared on the porous substrate 10. Sample H is shown in FIGS. 8 and 9. FIG. 8 shows the film top 23 and FIG. 9 shows the fractured edge of Y/Zr=16/84 film oxidized at 700° C. for 2 h. The surface was not smooth and many large island-shaped grains were found. Although sample H showed good fluid-separation, the rough surface may limit achievable minimum film thickness. The inhomogeneous surface could be due to the high Ar pressure to retain plasma on the complex target surface with the high contact resistance between Y-pellet and Zr target.

FIG. 10 shows the backside-view of the continuous film 20 of Sample E that was in contact with the 20 nm-type substrate 10. To have unobstructed access to the bottom said of the continuous film 20, the substrate 10 was etched out with 1N—NaOH solution. The bottom side 24 was different from the top surface 23 of the same sample E. The bottom side displayed circle-shaped islands with diameter ranging from 50 nm to 120 nm on the whole surface, suggesting that the thin film covering the top of the substrate—s 10 pores was swallowed into the pores.

Figure 11B:
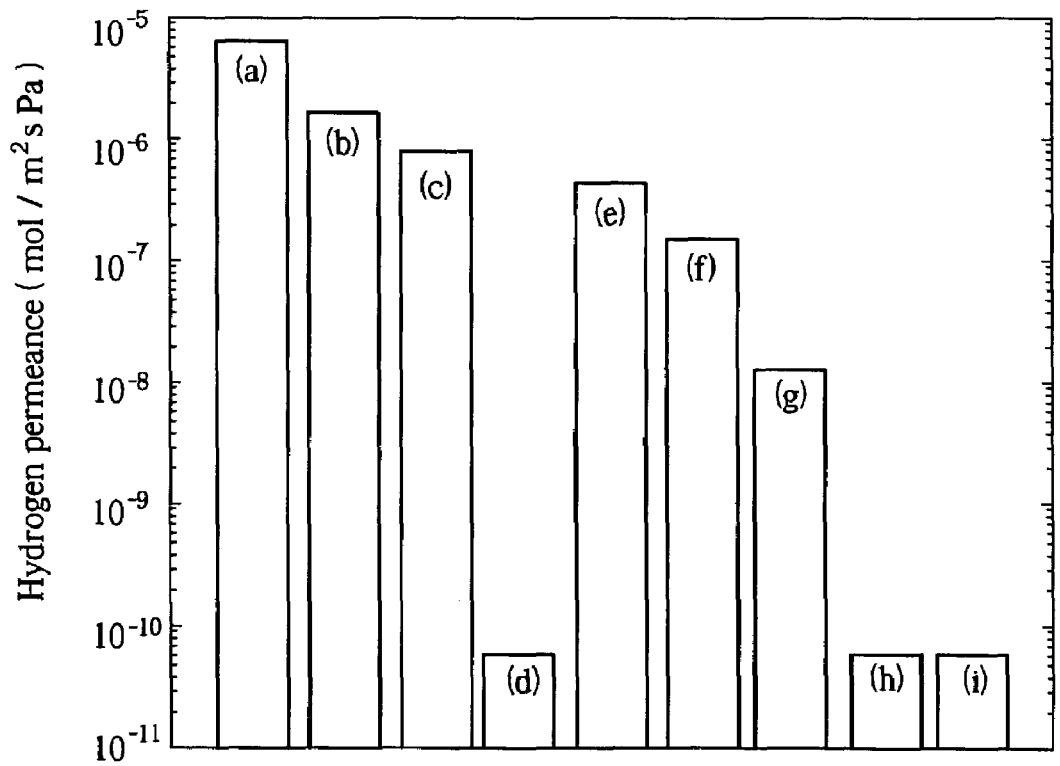

Fluid impermeability was tested in a hydrogen permeation test in which the hydrogen permeance was measured for the oxidized Y—Zr thin films 20 at 0.1 MPa hydrogen pressure. The results are illustrated in FIG. 11b. The permeance of the substrate 10 without heating (column (a) for 200 nm-type substrate 10 and column (e) for 20 nm-type substrate 10) and with heating at 700° C. for 2 h (column (b), for 200 nm-type substrate 10 and column (f) for 20 nm-type substrate 10) are again shown for comparison. The permeance for sample D (column (c)) slightly decreased to $7.49 \times 10^{-7}$ mol/m$^2 \cdot$s$\cdot$Pa. The continuous thin film 20 of sample D did not demonstrate sufficient fluid-separation compared to the low permeance value in the 35 nm-thick Alumina thin film on 200 nm-type substrate 10. However, the permeance for the sample F (column (d)) dropped to $7.44 \times 10^{-11}$ mol/m$^2 \cdot$s$\cdot$Pa, which was below the measuring limit. This implies that the 250 nm-thick film 20 on 20 nm-pore-sized substrate 10 is enough to work as a gas separation layer. That is, the thickness of 50 nm deposited with DC-magnetron sputtering in a substantially perpendicular deposition direction was insufficient to form a continuous film 20 across the pores of the 200 nm-type porous substrate 10.

The samples C, G, and E fabricated on top of the 20 nm-type substrate 10, displayed small fluid permeance values as indicated with columns (g), (h) and (i). Fluid permeance for sample E and G (columns (h) and (i)) was below measurement resolution and could not be detected (illustrated in FIG. 11b as $7.44 \times 10^{-11}$ mol/m$^2 \cdot$s$\cdot$Pa, which was the lower measuring limit). Since the measured minimal hydrogen permeance for initial driving of an SOFC was about $4.5 \times 10^{-9}$ mol/m$^2 \cdot$s$\cdot$Pa, the obtained results strongly support the high possibility for direct application in low-temperature SOFCs.

The minimum film thickness for continuous films 20 of YSZ on 20 nm-type porous substrate 10 is estimated with 6.61 nm by use of Eq[1,2] for $\Delta P$=0.1 MPa at room temperature. The difference between the reported mechanical data for 8YSZ sheet and thin films may be reasonably applied to adjust the minimum thickness estimation.

Figure 15:
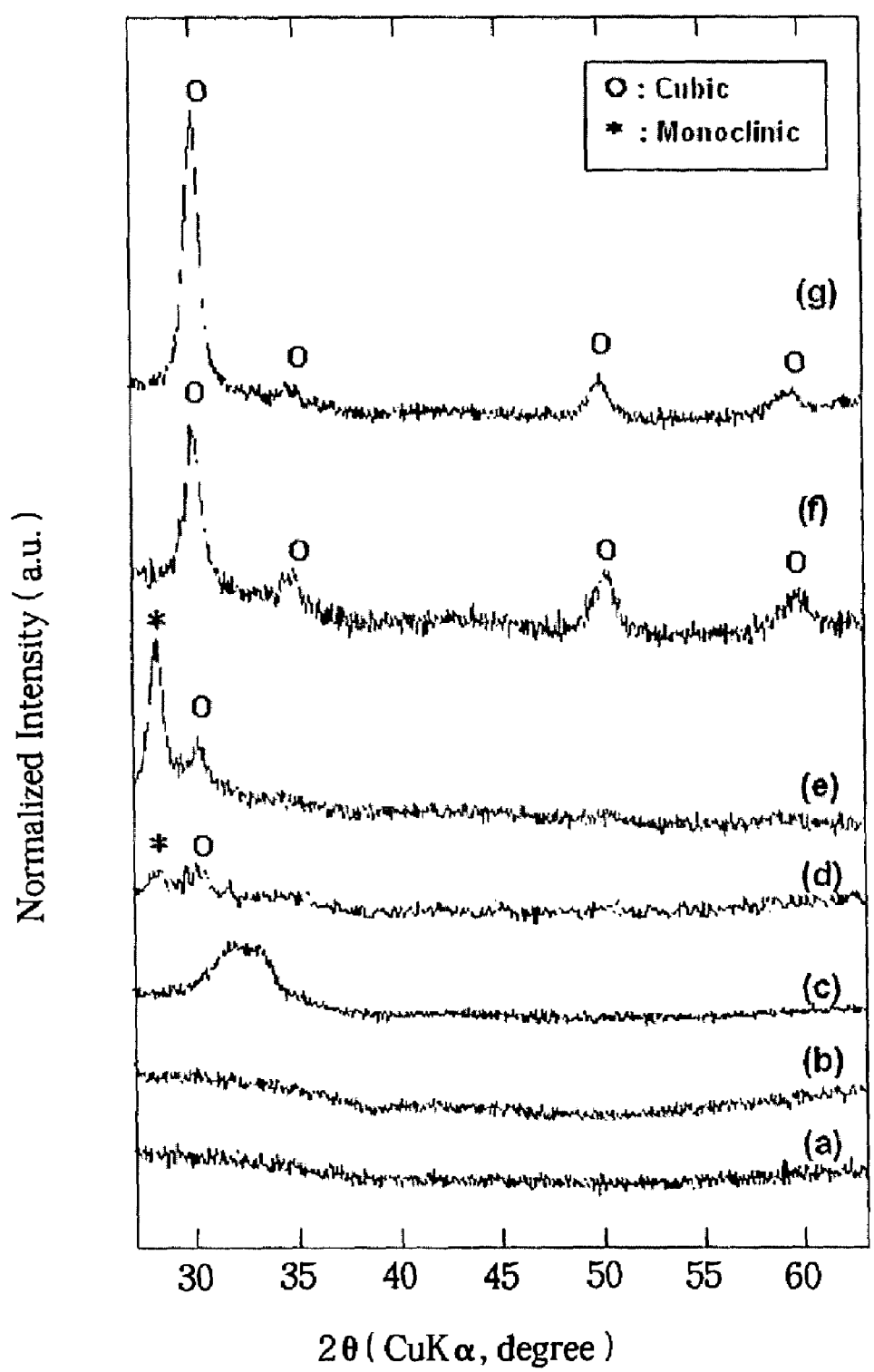
FIG. 15 depicts X-ray normalized reflectometric measurement plots at various stages during fabrication of the continuous film in accordance with a preferred embodiment.
Figure 16:
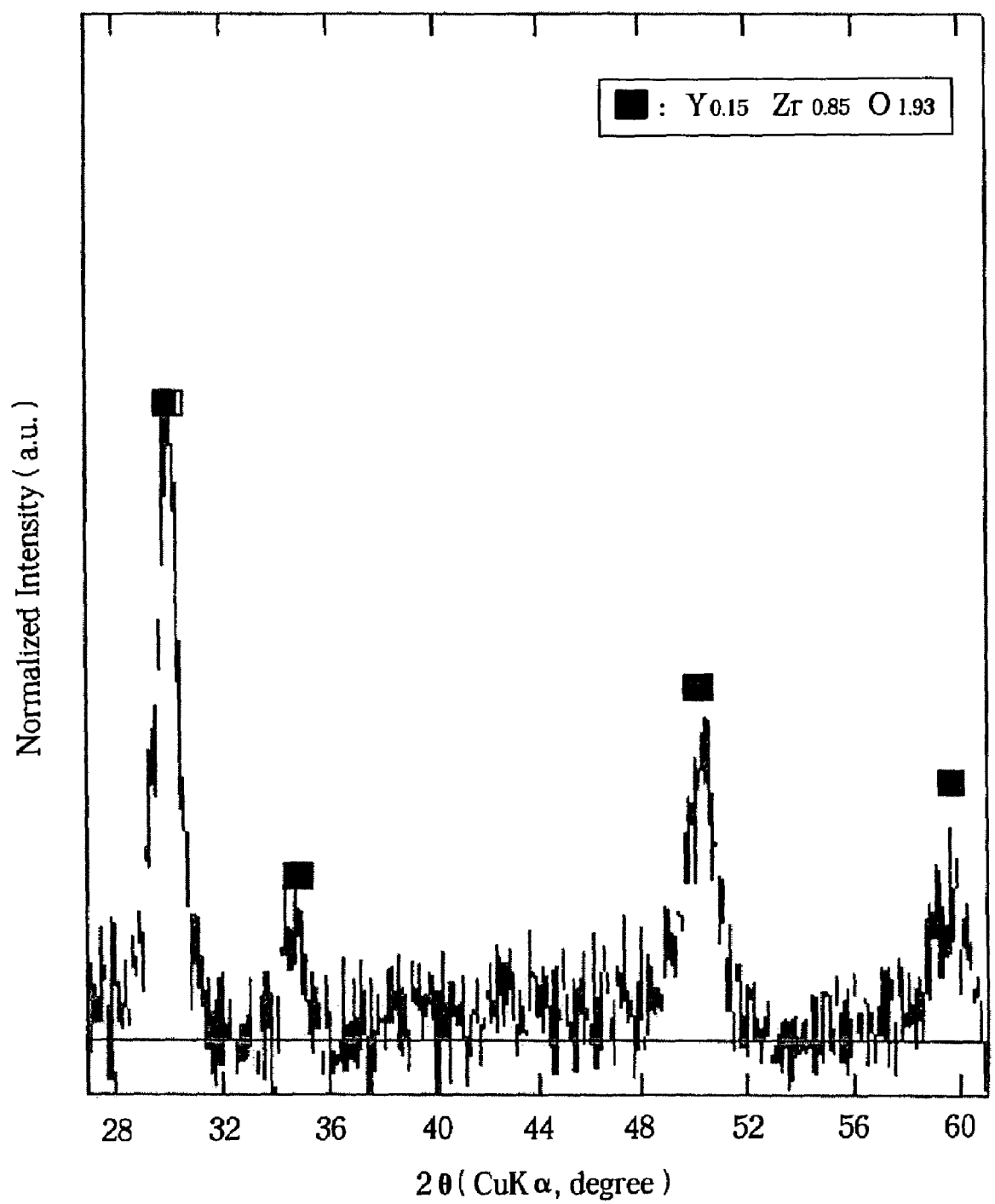
FIG. 16 shows a base line compensated X-ray reflectometric measurement plot of a final continuous film in accordance with a preferred embodiment.

Oxidation and Phase Development of YSZ Thin Films 20 was observed using again XRD patterns obtained with sample C. The measurement results are illustrated in FIG. 15. There was no distinct crystalline peak in the pattern at room temperature (graph (c)) and at 500° C. (graph (d)) for sample E. However, the color of thin film changed from metal silver to glassy transparent during oxidation at 500° C. for 10 h. At 700° C., a clear crystalline phase was detected. As mentioned above, the crystalline phase for Y—Zr film was easily achieved at a lower temperature than Alumina thin film due to its inherent high oxygen diffusivity. The observed crystalline peaks matched a mixed phase of cubic and monoclinic (graph (e)) that had been reported as a crystalline phase for a solid solution of $Y_2O_3$ and $ZrO_2$ having a composition in the range of about 3/97~15.6/83.4 of Y/Zr composition. By increasing the Yttrium concentration from 3 at % (sample E, graph (e)) to 16 at % (sample H, graph (f)) and 43 at % (sample G, graph (g)), the monoclinic phase in oxidized thin film 20 disappeared and clear cubic single phase was achieved. The relative intensity displayed in FIG. 16 was estimated from the fitted peaks, matched well with the relative peak intensity from reported data for bulk polycrystalline $Y_{0.15}Zr_{0.85}O_{1.93}$ indicating that the film had no preferred orientation.

The crystalline YSZ could be easily obtained by oxidation at 500° C.~700° C., a quite lower temperature than Alumina thin film. Oxidation of the deposited Y/Zr alloy material 4 occurs at very low temperatures in a relatively short period compared to deposited Alumina material 4. As a favorable result, the inventive process has also significance as a low-temperature processing for oxide thin films, besides its preferred application for fabricating ultra-thin film with nano-size conductivity effects as described in more detail in the below.

Figure 13:
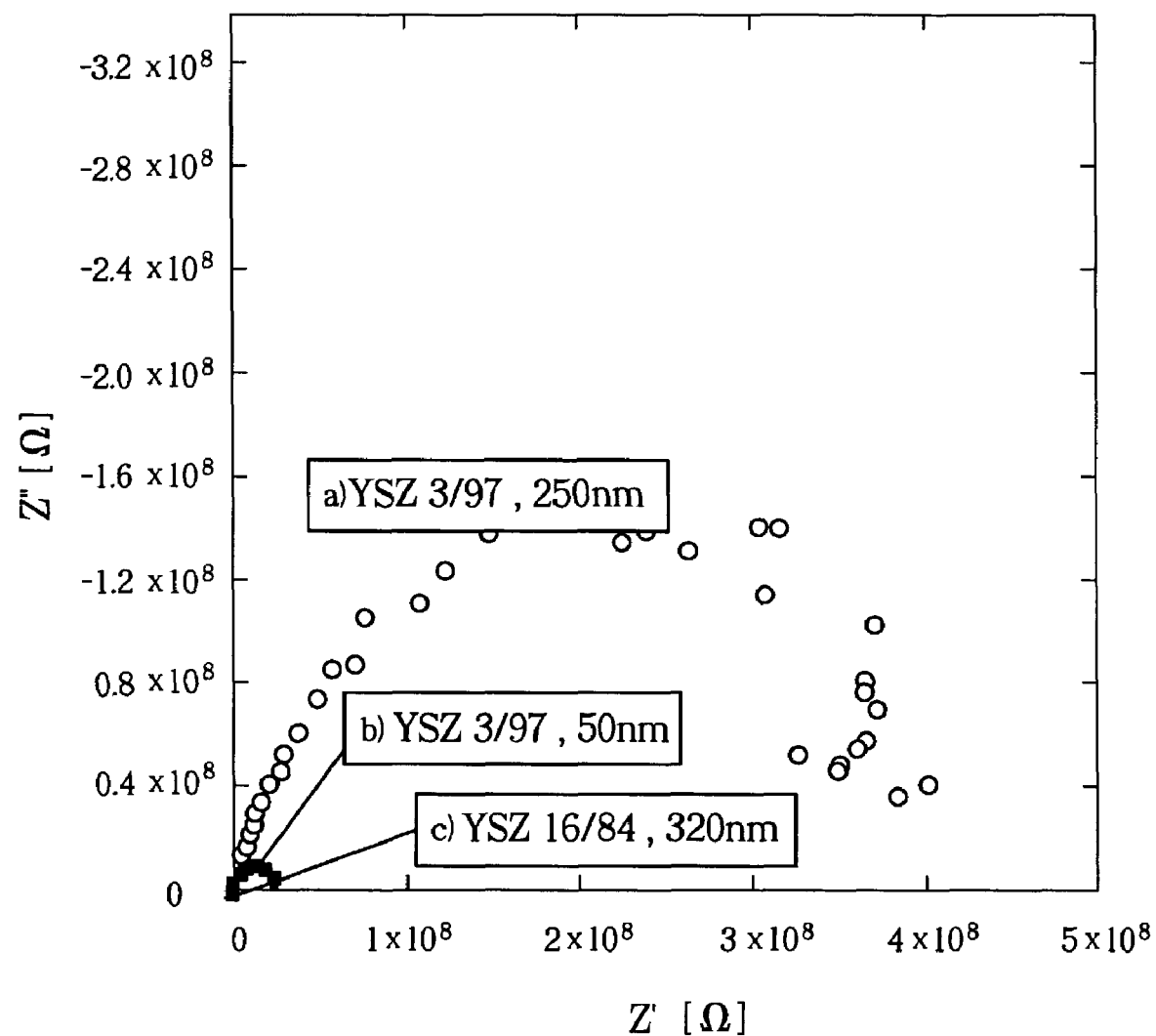
FIG. 13 illustrates measurement results obtained with the test setup of FIG. 12.
Figure 14:
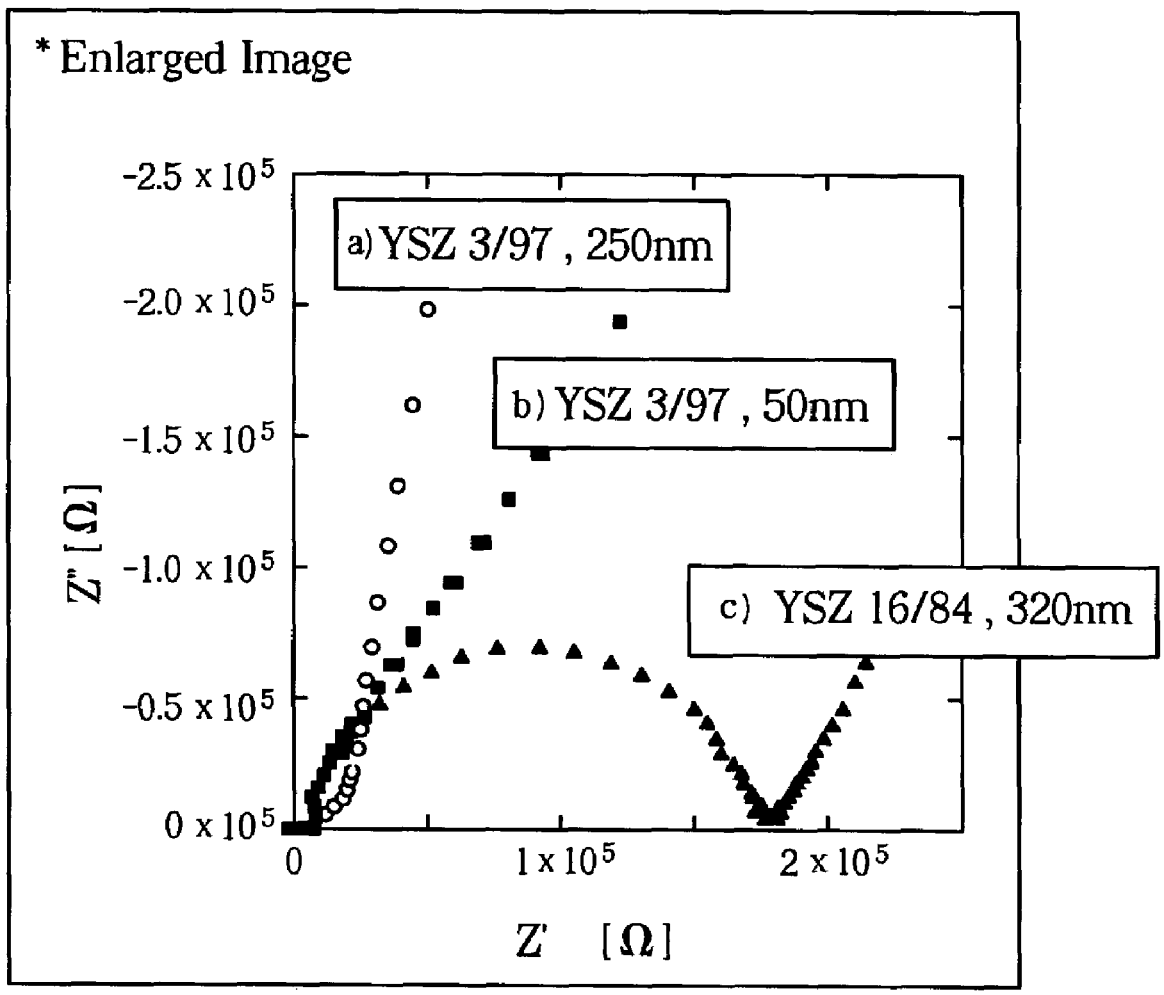
FIG. 14 shows an enlarged portion of the graph of FIG. 13.

Conductivity of YSZ thin Films was measured with Nyquist plots shown in FIGS. 13 and 14. Measurements were taken for sample E ((a) ○, Y/Zr=3/97, thickness: 250 nm), sample C ((b) ■, Y/Zr=3/97, thickness: 50 nm) and sample H ((c) △, Y/Zr=16/84, thickness: 320 nm). The obtained obvious semicircles represent resistance of the YSZ thin films 20 on porous substrates 10. A small resistance component was associated to the electrode-solution 126. About 6000Ω resistance at the left ends of the semicircles matched well with the measured electrode resistance of 0.03N—NaCl. As the thickness was reduced from 250 nm (sample E) to 50 nm (sample C), the resistance decreases from $3.67 \times 10^8 \Omega$ (FIG. 13, 14(a)) to $2.50 \times 10^7 \Omega$ (FIG. 13, 14(b)). A large decrease of resistance to $1.79 \times 10^5 \Omega$ (sample H, FIG. 13, 14(c)) was observed by changing composition from Y/Zr=3/97 to Y/Zr=16/84 in spite of the film thickness being thicker (~320 nm) than the other two samples.

The ionic conductivity of samples E and C, which had substantially the same composition (Y/Zr=3/97) and different thickness (50 nm and 250 nm), calculated from the ionic resistances obtained from the nyquist plots (FIG. 13, 14(b) and (c)) were $4.07 \times 10^{-12}$ S/cm and $1.11 \times 10^{-12}$ S/cm respectively. These results showed almost the same value. However, the conductivity for sample H (FIG. 13, 14(a)) with a composition of increased yttrium concentration (Y/Zr=16/84) showed a much higher value of $3.42 \times 10^{-9}$ S/cm. All the conductivities obtained for the thin films 20 are indicated in FIG. 17.

Figure 17:
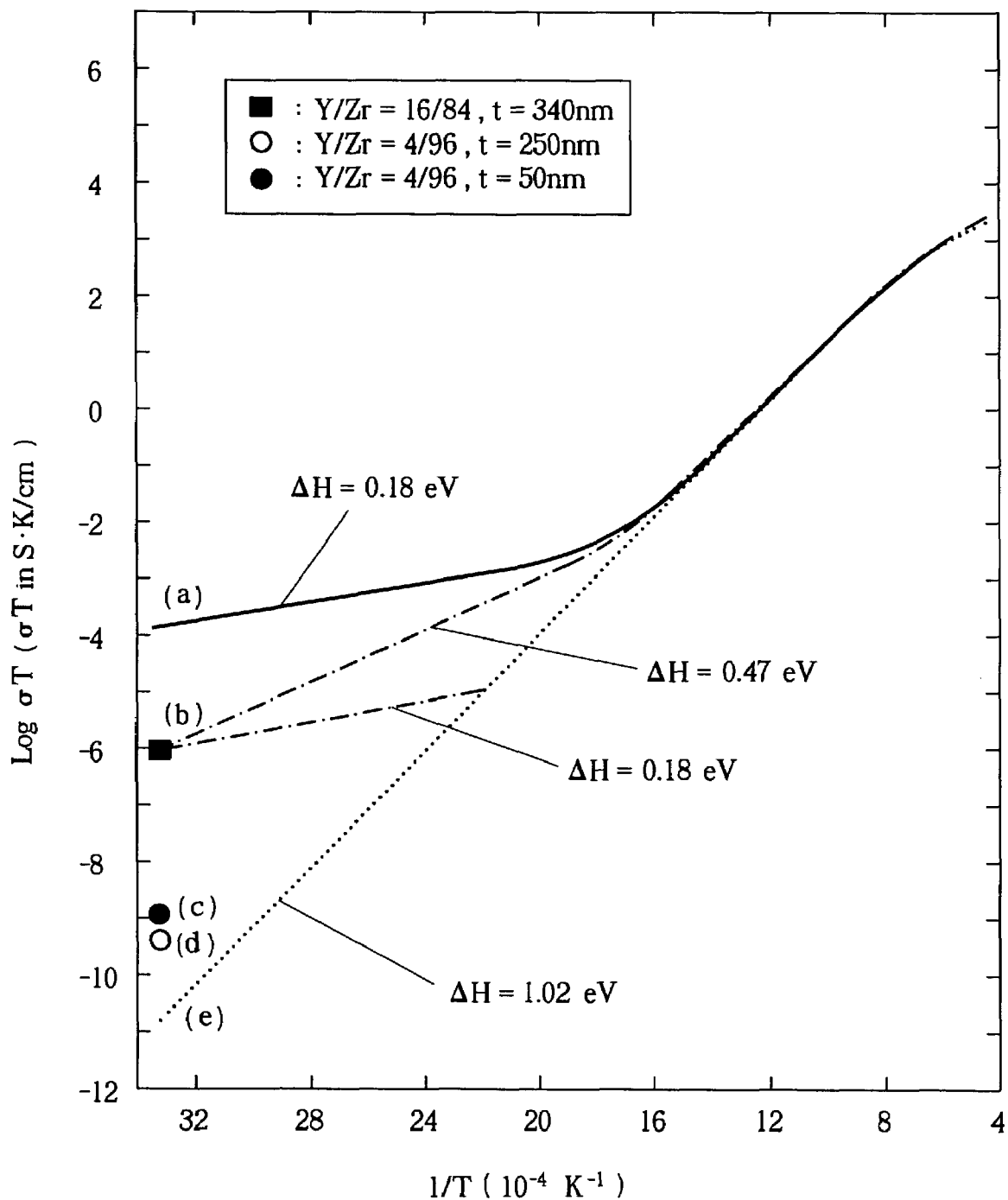
FIG. 17 shows ionic conductivity in dependence of working temperature for continuous films with varying thickness made of various deposited materials.
Figure 18:
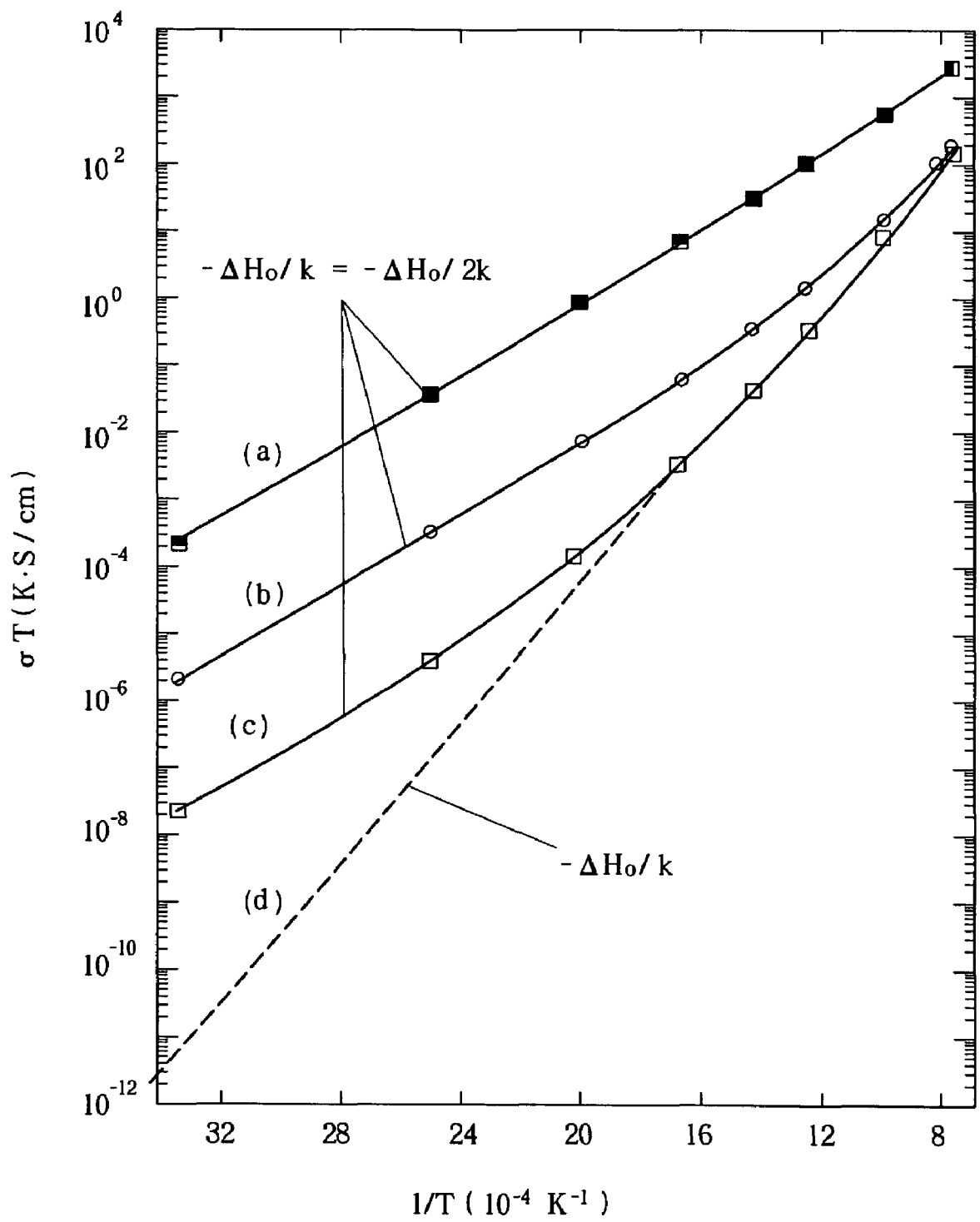
FIG. 18 graphically illustrates the bending of Arrhenius line by dislocation paths having a given activation energy and having varying densities.

As can be seen in FIG. 17, the conductivity values for thin films 20 are not on the extrapolated line of the reported Arrhenius plot of 8YSZ (FIG. 17(e)). All the measured conductivity values are largely shifted to the estimated Arrhenius plot (FIG. 17(a)) with low activation energy of only 0.18 eV. FIG. 17(a) is a reference graph suggested in the prior art based on the fast oxygen diffusion through grain boundaries and its large contribution to lower the activation energy ($\Delta H$) for oxygen ionic conduction. Since the ionic conductivity term ($\sigma$) is proportional to $\exp(-\Delta H/kT)$, the contribution of lowered $\Delta H$ to $\sigma$ exponentially increases with a decrease of temperature. As all the conductivity of the samples was measured just at room temperature, it is difficult to define activation energy. However, it is reasonable to say that $\Delta H$ for sample H (FIG. 15(b)) possibly is in the range of 0.18 eV to 0.47 eV, which is much smaller than 1.02 eV (FIG. 15(e)). That is, if the estimated $\Delta H$ value of 0.18 eV is exact and the activation energy for the defect-free YSZ is exactly the same as that of the grains in the obtained thin films 20, defect density should be the only variable to change the absolute conductivity.

The bending Arrhenius plot at low temperature and change of the absolute conductivity can be simulated with a model with edge dislocations. The ratio of the conductivity of YSZ single crystal films having penetrating edge dislocation paths with different densities having an activation energy $\Delta H_d = \Delta H_o/2$ to the conductivity of bulk YSZ single crystal having an activation energy $\Delta H_o$ is calculated by the following equations:

$$\phi = \pi \varphi^2 \cdot \delta \quad [5]$$

$$D_d = D_o \cdot (1-\phi) \cdot \exp(-\Delta H_o/kT) + D_o \cdot \phi \cdot \exp(-\Delta H_d/kT) \quad [6]$$

$$D_b = D_o \cdot \exp(-\Delta H_o/kT) \quad [7]$$

therefore, $$D_d/D_b = D_o \cdot [(1-\varphi) \cdot \exp(-\Delta H_o/kT) + \quad [8]$$
$$\varphi \cdot \exp(-\Delta H_d/kT)]/[D_o \cdot \exp(-\Delta H_o/kT)]$$

$$= (1-\varphi) + \varphi \cdot \exp[(-\Delta H_d + \Delta H_o)/kT] \quad [9]$$

where, $\phi$: volume fraction of dislocations
  $\varphi$: radius of dislocation
  $\delta$: dislocation density
  $D_b$: diffusivity of 8YSZ single crystal
  $D_d$: diffusivity of 8YSZ with dislocations
  k: Boltzmann's constant
  T: temperature Several assumption are used in the estimation:
(i) all the dislocations are assumed as edge-dislocations, and as arranged in parallel in the current-flow direction penetrating thin films;
(ii) the shape of dislocation is assumed as pipe with circular crosssection, and the diameter of dislocation as $3\sqrt{2}/4$ times of lattice parameter (a) because the dislocation diameter ($2\varphi$) is supposed to be in the range of $\sqrt{2}a/2 < 2\varphi < \sqrt{2}a$ for the $a/\sqrt{2} < 110 > \{100\}$ dislocation system;
(iii) the diffusivity ($D_o$) is assumed to have the same value in bulk and in dislocations because it depends on several constants that are independent with activation energy. The $D_{od}$, that is $D_o$ of 8YSZ with dislocations, is expressed as $Ar^2 vN_v \cdot \exp[(\Delta S_o + \Delta S_d)/k]$, where all the variables are constants at the given temperature, that is, a proportional constant (A), atomic oscillation frequency (v), vacancy density ($N_v$), and entropy ($\Delta S$). Although the absolute value of the conductivity will be slightly changed by applying $D_{od}$ into the estimation for Eq. [8], that is, $D_d/D_b = D_o \cdot [(1-\phi) \cdot \exp(-\Delta H_o/kT) + \phi \cdot \exp(-\Delta H_d/kT)]/[D_o \cdot \exp(-\Delta H_o/kT)]$. However, the slope of the conductivity plot, $-\Delta H/k$, in the lower temperature region is not affected.

The Arrhenius plot of YSZ with dislocations estimated with Eq. [9] and extrapolated Arrhenius plot of a reported 8YSZ single crystal are bent as shown in FIG. 17(a)–(c), indicating a great increase of conductivity at temperatures below 500° C. With increasing dislocation density, the temperature to deviate from FIG. 17(d) increases, accompanying a significant increase of absolute conductivity. Since the grain boundary 6 itself may be theoretically expressed as bundles of dislocations, the estimation performed for a dislocation effect on the conductivity at low temperature can be one of reasonable explanations for the extraordinary increase of ionic conductivity at low temperature, especially in thin films with nanometer-sized grains 2, which contain a large volume fraction of grain boundaries 6. Parasitic capacitances may build up where ions eventually have to bridge across adjacent grain boundaries 6 perpendicularly oriented to the ions' path from one thin film surface to the opposing surface. To minimize the degrading effect of parasitic capacitances, it is desirable to deposit the material 4 in a fashion that grains 2 predominantly form in a single plane. Consequently, grain boundaries 6 extend substantially continuously from surface-to-surface and provide highly conductive pathways substantially free of parasitic capacitances. The experimental results suggest that heat treatment following oxidation may be adjusted to tune recombination of grain boundaries 6 for an optimized balance between low temperature ion conductivity and fluid impermeability.

It will be clear to a person of average skill in the art that the preferred embodiments described in the above may be altered in many ways without departing from the scope of the invention. Particularly, other porous substrates 10 such as porous silicon may be used with deposition materials 4 that exhibit oxidation expansion. Also, other well-known ceramic material with suitable ionic conductivity may be fabricated in a fashion similar as described in the above for YSZ. Such ceramic may be for example, gadolinium doped ceria.

Ionic conductivity of the continuous film 20 may be further improved by fabricating continuous surface-to-surface dislocations into the continuous film 20. For a more detailed description it is referred to the concurrently filed and cross referenced application titled "Solid oxide electrolyte with ion conductivity enhancement by dislocation".

Figure 19:
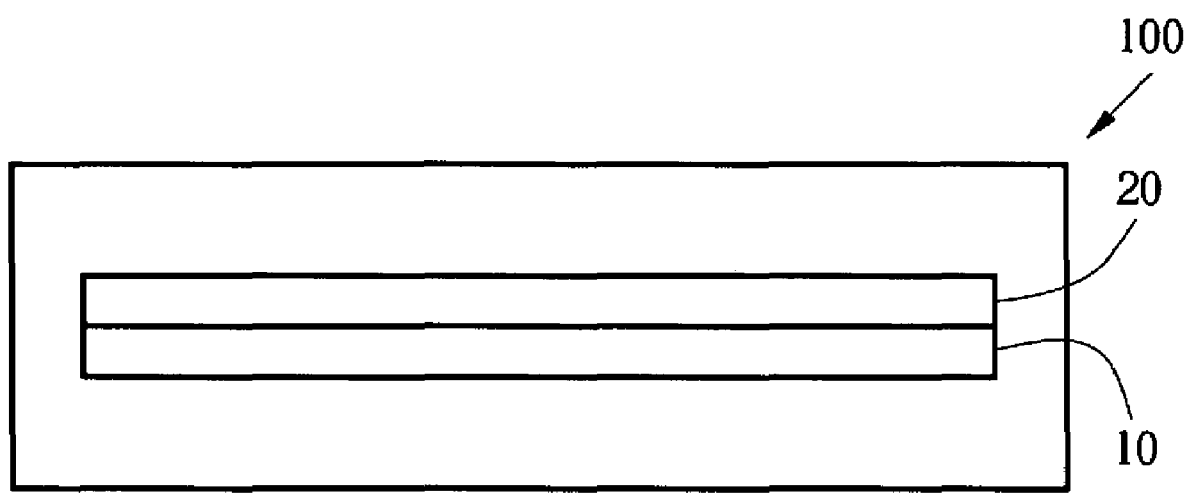
FIG. 19 shows a device having a continuous film on a porous substrate in accordance with the present invention.

Referring to FIG. 19 and the case, where the continuous film 20 operates as an electrolyte membrane in a device 100 such as a fuel cell or a gas sensor, the porous substrate 10 may be made electrically conductive in a well-known fashion like, for example through electroplating and/or doping. The porous substrate 10 may also be a metallic substrate.

Accordingly, the scope of the invention described in the specification above is set forth by the following claims and their legal equivalent:

What is claimed is:

1. A method for fabricating a continuous film on a porous substrate, said method comprising:
  a. selecting a deposition material having a oxidation expansion ratio, wherein an in-plane portion of the oxidation expansion ratio is equal to the second power of the third root of the oxidation expansion ratio;
  b. depositing said deposition material with a deposition height and deposition density on top of said porous substrate, said deposition material being in an unoxidized condition;
  c. oxidizing said deposition material on top of said substrate whereby said deposition material is converted into an oxidized material being spatially expanded with respect to said deposition material;
  wherein said deposition density is greater than or equal to the inverse of said in-plane portion of the oxidation expansion ratio;
  wherein said deposition height and said deposition density are selected in conjunction with said spatial oxidation expansion such that during said oxidizing a substantially void-free film is formed on top of said substrate; and
  d. heat treating said void-free film to recombine said oxidized material into said continuous film.

2. The method of claim 1, wherein said deposition material is selected such that following said oxidizing said oxidized material is an ion conducting electrolyte and such that said continuous film is substantially fluid impermeable.

3. The method of claim 2, wherein said deposition material is an yttria stabilized zirconia.

4. The method of claim 1, wherein said porous substrate is made of an oxide.

5. The method of claim 4, wherein said porous substrate is made of anodized alumina.

6. The method of claim 1, wherein on said top of said porous substrate are pores with a pore diameter of less than 200 nm, said continuous film having a thickness of less than 1 μm and having a hydrogen permeability of less than 10e–10 mol/m2sPa at room temperature.

7. The method of claim 1, wherein said continuous film has a hydrogen permeability of less than 10e–10 mol/m2sPa at room temperature and an ionic area resistance of less than 200 ohm at a temperature of 250° C. for a thickness of said continuous film of about 1 μm and for said continuous film being made of yttria stabilized zirconia.

8. The method of claim 1, wherein said continuous film is an electrolyte membrane for a fuel cell.

9. The method of claim 1, wherein said depositing is performed with DC magnetron sputtering.

10. The method of claim 1, wherein said porous substrate includes pores having a diameter between 80 nm and 200 nm prior to said heat treating.

* * * * *